US007226999B2

(12) United States Patent
Andersen et al.

(10) Patent No.: US 7,226,999 B2
(45) Date of Patent: *Jun. 5, 2007

(54) PROTEIN C OR ACTIVATED PROTEIN C-LIKE MOLECULES

(75) Inventors: Kim Vilbour Andersen, Broenshoej (DK); Anders Hjelholt Pedersen, Lyngby (DK); Per Ola Freskgaard, Vellinge (SE)

(73) Assignees: Maxygen ApS, Hoersholm (DK); Maxygen Holdings Ltd., Grand Caymen (KY)

( * ) Notice: Subject to any disclaimer, the term of this patent is extended or adjusted under 35 U.S.C. 154(b) by 0 days.

This patent is subject to a terminal disclaimer.

(21) Appl. No.: 11/004,111

(22) Filed: Dec. 3, 2004

(65) Prior Publication Data

US 2005/0095668 A1    May 5, 2005

Related U.S. Application Data

(63) Continuation of application No. 09/997,623, filed on Nov. 29, 2001, now Pat. No. 6,933,367, which is a continuation-in-part of application No. 09/978,917, filed on Oct. 17, 2001, now abandoned.

(60) Provisional application No. 60/300,154, filed on Jun. 21, 2001, provisional application No. 60/242,268, filed on Oct. 18, 2000.

(30) Foreign Application Priority Data

Oct. 18, 2000  (DK) ................ PA 2000 01560
Jun. 21, 2001  (DK) ................ PA 2001 00970

(51) Int. Cl.
  A61K 35/14   (2006.01)
  A61K 38/48   (2006.01)
  C07K 14/00   (2006.01)

(52) U.S. Cl. ............ 530/380; 530/395; 530/350; 514/12; 536/23.5; 435/226; 435/320.1; 435/325; 424/94.64

(58) Field of Classification Search ........... 530/395, 530/350, 380; 536/23.5; 435/226, 320.1, 435/325; 424/94.64; 514/12
See application file for complete search history.

(56) References Cited

U.S. PATENT DOCUMENTS

| 4,775,624 A | 10/1988 | Bang et al. |
| 4,904,584 A | 2/1990 | Shaw |
| 4,959,318 A | 9/1990 | Foster et al. |
| 4,968,626 A | 11/1990 | Foster et al. |
| 4,992,373 A | 2/1991 | Bang et al. |
| 5,041,376 A | 8/1991 | Gething et al. |
| 5,073,609 A | 12/1991 | Foster et al. |
| 5,151,268 A | 9/1992 | Bang et al. |
| 5,196,322 A | 3/1993 | Bang et al. |
| 5,225,537 A | 7/1993 | Foster |
| 5,270,040 A | 12/1993 | Bang et al. |
| 5,270,178 A | 12/1993 | Gerlitz et al. |
| 5,302,529 A | 4/1994 | Foster et al. |
| 5,358,932 A | 10/1994 | Foster et al. |
| 5,453,373 A | 9/1995 | Gerlitz et al. |
| 5,460,953 A | 10/1995 | Gerlitz et al. |
| 5,516,650 A | 5/1996 | Foster et al. |
| 5,648,254 A | 7/1997 | Mulvihill et al. |
| 5,753,224 A | 5/1998 | Foster et al. |
| 5,766,921 A | 6/1998 | Foster et al. |
| 5,837,843 A | 11/1998 | Smirnov et al. |
| 5,847,085 A | 12/1998 | Esmon et al. |
| 6,933,367 B2 * | 8/2005 | Andersen et al. ......... 530/380 |

FOREIGN PATENT DOCUMENTS

| EP | 0 370 205 A2 | 5/1990 |
| EP | 0 575 054 A2 | 12/1993 |
| JP | 3072877 | 3/1991 |
| JP | 08-092294 | 9/1996 |
| WO | WO 89/05824 A1 | 6/1989 |
| WO | WO 98/44000 A1 | 10/1998 |
| WO | WO 99/20767 A1 | 4/1999 |
| WO | WO 00/26230 A1 | 5/2000 |
| WO | WO 00/26354 A1 | 5/2000 |
| WO | WO 00/54787 A1 | 9/2000 |
| WO | WO 00/66753 A2 | 11/2000 |
| WO | WO 0066754 A1 | 11/2000 |

(Continued)

OTHER PUBLICATIONS

Colpitts, Tracey L. et al., "Binding of Calcium to Individual γ-Carboxyglutamic Acid Residues of Human Protein C", *Biochemistry*, 1995, 34, 2424-2430.

(Continued)

*Primary Examiner*—Chih-Min Kam
(74) *Attorney, Agent, or Firm*—Joanne R. Petithory; Norman J. Kruse

(57) ABSTRACT

The present invention relates to novel conjugates between polypeptide variants of protein C and a non-polypeptide moiety, such as PEG or sugar moieties. In particular, the present invention provides novel protein C conjugates having an increased resistance to inactivation by e.g. human plasma and $\alpha_1$-antitrypsin. Consequently, such conjugates have an increased in vivo half-life. Preferred examples include protein C conjugates, wherein at least one additional in vivo N-glycosylation site has been introduced. The conjugates of the invention are useful for treating a variety of diseases, including septic shock.

16 Claims, 4 Drawing Sheets

FOREIGN PATENT DOCUMENTS

| | | |
|---|---|---|
| WO | WO 01/36463 A2 | 5/2001 |
| WO | WO 01/57193 A2 | 8/2001 |
| WO | WO 01/59084 A1 | 8/2001 |

OTHER PUBLICATIONS

Friedrich, Ute. et al., "Secondary Substrate-binding Exosite in the Serine Protease Domain of Activated Protein C Important for Cleavage at Arg-506 but Not at Arg-306 in Factor Va", *The Journal of Biological Chemistry*, 2001, vol. 276, No. 25:23105-23108.

Friedrich, Ute et al., "Structural and Energetic Characteristics of the Heparin-binding Site in Antithrombotic Protein C", *The Journal of Biological Chemistry*, 2001, vol. 276, No. 26:24122-24128.

Gale, Andrew J. et al., "The autolysis loop of activated protein C interacts with factor Va and differentiates between the Arg506 and Arg306 cleavage sites", *Blood*, 2000, vol. 96, No. 2:585-593.

Gale, Andrew J. et al., "Nonenzymatic anticoagulant activity of the mutant serine protease Ser360Ala-activated protein C mediated by factor Va" *Protein Science*, (1997), 6:132-140.

Geng, Jie-Ping et al., "Functional Consequences of Mutations in Amino Acid Residues that Stabilize Calcium Binding to the First Epidermal Growth Factor Homology Domain of Human Protein C", *Thrombosis and Haemostatis*, (1990) 76:720-728.

Gerlitz, Bruce et al., "Mutation of Protease Domain Residues Lys37-39 in Human Protein C Inhibits Activation by the Thrombomodulin-Thrombin Complex without Affecting Activation by Free Thrombin", *The Journal of Biological Chemistry*, 1996, vol. 271, No. 37:22285-22288.

Hallam, Paula J. et al., "A novel missense mutation (Thr176→Ile) at the putative hinge of the neo N-terminus of activated protein C", *Hum Genet*, (1995) 95:447-450.

Holly, Rick D. et al., "Resistance to inhibition by α-1Anti-Trypsin and Species Specificity of a Chimeric Human/Bovine Protein C", *Biochemistry*, (1994) 33:1876-1880.

Jhingan, Ashish et al., "The Activities of Recombinant γ-Carboxyglutamic-Acid-Deficient Mutants of Activated Human Protein C toward Human Coagulation Factor Va and Factor VIII in Purified Systems and in Plasma", *Biochemistry*, (1994) 33:1869-1875.

McDonald, John F. et al., "Comparison of Naturally Occurring Vitamin K-Dependent Proteins: Correlation of Amino Acid Sequences and Membrane Binding Properties Suggests a Membrane Contact Site", *Biochemistry*, (1997) 36:5120-5127.

Mesters, Rolf M. et al., "A Novel Exosite in the Light Chain of Human Activated Protein C Essential for Interaction with Blood Coagulation Factor Va", *Biochemistry*, (1993) 32:12656-12663.

Mesters, Rolf M. et al., "Identification of a Sequence of Human Activated Protein C (Residues 390-404) Essential for Its Anticoagulant Activity", *The Journal of Biological Chemistry*, 1991, vol. 266, No. 36:24514-24519.

Nishioka, Junji et al., "The Gla26 Residue of Protein C is Required for the Binding of Protein C to Thrombomodulin and Endothelial Cell Protein C Receptor, but not to Protein S and Factor VA", *Thrombosis and Haemostasis*, (1996) 75:275-282.

Öhlin, Ann-Kristin et al., "Proteolytic Formation and Properties of a Fragment of Protein C Containing the γ-Carboxyglutamic Acid Rich Domain and the EGF-like Region", *Biochemistry*, (1990) 29:644-651.

Rezaie, Alireza, R. "Role of Residue 99 at the S2 Subsite of Factor Xa and Activated Protein C in Enzme Specificity", *The Journal of Biological Chemistry*, 1996, vol. 271, No. 39:23807-23814.

Rezaie, Alireza, R. "Calcium Inhibition of the activation of protein C by thrombin Role of the P3 and P3' residues", *Eur. J. Biochem.*, (1994) 223:575-579.

Rezaie, Alireza, R. "Vitronectin Functions as a Cofactor for Rapid Inhibition of Activated Protein C by Plasminogen Activator Inhibitor-1", *The Journal of Biological Chemistry*, May 11, 2001, vol. 276, No. 19:15567-15570.

Rezaie, Alireza, R. et al., Conversion of Glutamic Acid 192 to Glutamine in Activated Protein C Changes the Substrate Specificity and Increases Reactivity toward Macromolecular Inhibitors, *The Journal of Biological Chemistry*, 1993, vol. 268, No. 27:1 9943-19948.

Rintelen, Claudia et al., "Anticoagulant Dysfunction of Human Arg352Trp-Activated Protein C Caused by Defective Factor Va Inactivation", *Thrombosis and Haemostasis*, (2001) 85:274-279.

Shen, Lei et al., "Enhancing the Activity of Protein C by Mutagenesis To Improve the Membrane-Binding Site: Studies Related to Proline-10", *Biochemistry*, 1997, vol. 36, No. 51:16025-16031.

Shen, Lei et al., "Enhancement of Human Protein C Function by Site-directed Mutagenesis of the γ-Carboxyglutamic Acid Domain", *The Journal of Biological Chemistry*, 1998, vol. 273, No. 47:31086-31091.

Shen, Lei et al., "Interspecies Loop Grafting in the Protease Domain of Human Protein C Yielding Enhanced Catalytic and Anticoagulant Activity", *Thrombosis and Haemostasis*, (1999) 82:1078-1087.

Shen, Lei et al., "Tracking Structural Features Leading to Resistance of Activated Protein C to ∝ 1-antitrypsin", *Biochemistry*, (2000) 39:2853-2860.

Thariath, Abraham et al., "Highly conserved residue arginine-15 is required for the $Ca^{2+}$-dependent properties of the γ-carboxyglutamic acid domain of human anticoagulation Protein C and activated Protein C", *Biochem. J.*, (1997) 322:309-315.

Zhang, Li et al., "Role of Individual γ-Carboxyglutamic Acid Residues of Activated Human Protein C in Defining its In Vitro Anticoagulant Activity", *Blood*, 1992, vol. 80, No. 4:942-952.

Zhang, Li et al., "The Binding Energy of Human Coagulation Protein C to Acidic Phospholipid Vesicles Contains a Major Contribution from Leucine 5 in the γ-Carboxyglutamic Acid Domain", *The Journal of Biological Chemistry*, 1994, vol. 269, No. 5:3590-3595.

Zhang, Li et al., "Role of the Hexapeptide Disulfide Loop Present in the γ-Carboxyglutamic Acid Domain of Human Protein C in Its Activation Properties and in the in Vitro Anticoagulant Activity of Activated Protein C", *Biochemistry*, (1991) 30:6696-6704.

Pfeiffer, Gunter, et al., "Glycosylation of two recombinant human uterine tissue plasminogen activator variants carrying an additional N-glycosylation site in the epidermal-growth-factor-like domain" *Eur. J. Biochem.*, 219:331-348 (1994).

* cited by examiner

PROTEIN C OR ACTIVATED PROTEIN C-LIKE MOLECULES

CROSS-REFERENCE TO RELATED APPLICATIONS

This application is a continuation of U.S. application Ser. No. 09/997,623 filed Nov. 29, 2001, now U.S. Pat. No. 6,933,367, which is a continuation-in-part of U.S. application Ser. No. 09/978,917 filed Oct. 17, 2001, now abandoned, which claims priority to and benefit of U.S. Provisional Application Nos. 60/242,268 filed Oct. 18, 2000, and 60/300,154 filed Jun. 21, 2001, the disclosures of each of which is incorporated herein in their entirety for all purposes. Pursuant to 35 U.S.C. § 119(a)–(d), U.S. application Ser. No. 09/978,917 also claims priority to and benefit of Danish Patent Application Nos. PA 2000 01560 filed Oct. 18, 2000, and PA 2001 00970 filed Jun. 21, 2001, the disclosures of each of which is incorporated herein in their entirety for all purposes.

COPYRIGHT NOTIFICATION

Pursuant to 37 C.F.R. §1.71(e), Applicants note that a portion of this disclosure contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to novel conjugates between polypeptide variants of protein C and a non-polypeptide moiety, to means and methods for preparing such conjugates, to pharmaceutical compositions comprising such conjugates and the use of such conjugates in therapy, in particular for the treatment of a variety of coagulation disorders. The present invention also relates to the polypeptide part of the conjugates of the invention.

BACKGROUND OF THE INVENTION

Blood coagulation is a process consisting of a complex interaction of various blood components, or factors, which eventually give rise to a fibrin clot. Generally, blood components participating in the coagulation "cascade" are proenzymes or zymogens, i.e. enzymatically inactive proteins that are converted into an active form by action of an activator. Regulation of blood coagulation is largely accomplished enzymatically by proteolytic inactivation of the pro-coagulation factors Va and VIIIa achieved by activated protein C (APC) (Esmon, J Biol Chem 1989; 264; 4743–4746).

Protein C is a serine protease that circulates in the plasma as a zymogen with a half-life of approximately 7 hours and plasma levels are typically in the range of 3–5 mg/l. It is produced in vivo in the liver as a single chain precursor polypeptide of 461 amino acids. This polypeptide undergoes multiple post-translational modifications including a) cleavage of a 42 amino acid signal sequence; b) cleavage of lysine and arginine residues (positions 156 and 157) to make a two-chain inactive zymogen (a 155 amino acid light chain attached via a disulfide bridge to a 262 amino acid heavy chain); c) vitamin K-dependent carboxylation of nine glutamic acid residues of the light chain resulting in nine gamma-carboxyglutamic acid residues in the N-terminal region of the light chain; and d) carbohydrate attachment at four sites (one in the light chain and three in the heavy chain). Finally, the two-chain zymogen may be activated by removal of a dodecapeptide (the activation peptide) at the N-terminus of the heavy chain (positions 158–169) producing the activated protein C (APC).

Protein C is activated by limited proteolysis by thrombin in complex with thrombomodulin on the lumenal surface of the endothelial cell. As explained above, activation liberates a small 12 amino acid peptide (designated the activation peptide) from the N-terminal of the heavy chain. The APC has a half-life of approximately 15 minutes in plasma.

In the presence of its cofactor, protein S, APC proteolytically inactivates factors Va and VIIIa, thereby reducing thrombin generation (Esmon, Thromb Haemost 1993; 70; 29–35). Protein S circulates reversibly bound to another plasma protein, C4b-binding protein. Only free protein S serves as a cofactor for APC. Since C4b-binding protein is an acute phase reactant, the plasma levels of this protein varies greatly in many diseases and thus influence the anticoagulant activity of the protein C system.

The gene encoding human protein C maps to chromosome 2q13–q14 (Patracchini et al., Hum Genet 1989; 81; 191–192) spans over 11 kb, and comprises a coding region (exons II to IX) and a 5' untranslatable region encompassing exon I. The protein domains encoded by exons II to IX show considerable homology with other vitamin K-dependent coagulation proteins such as factor IX and X. Exon II codes for a signal peptide, while exon III codes for a propeptide and a 38 amino acid sequence containing 9 Glu residues. The propeptide contains a binding site for the carboxylase transforming the Glu residues into dicarboxylic acid (Gla) able to bind calcium ions, a step required for phospholipid binding and protein C anticoagulant activity (Cheung et al., Arch Biochem Biophys 1989; 274; 574–581). Exons IV, V and VI encodes a short connection sequence and two EGF-like domains, respectively. Exon VII encodes both a domain encompassing a 12 amino acid activation peptide released after activation of protein C by thrombin, and the dipeptide 156–157 which, when cleaved off, yields the mature two-chain form of the protein. Exons VIII and IX encodes the serine protease domain.

The complete amino acid sequence of the human protein C has been reported by Foster et al., PNAS. USA 1986; 82; 4673–4677 and includes a signal peptide, a propeptide, a light chain, a heavy chain and an activation peptide.

Protein C binds to the endothelial cell protein receptor (EPCR). Binding of APC to EPCR renders APC incapable of inactivating factor Va and VIIIa, whereas binding of protein C to EPCR apparently enhances the activation rate of protein C by the thrombin-thrombomodulin complex. The physiological importance of these interactions is presently unknown. Apparently the binding of protein C to EPCR is strictly dependent on the presence of the Gla domain in a phospholipid independent manner (Esmon et al., Haematologica 1999; 84; 363–368).

APC is inhibited in the plasma by the protein C inhibitor as well as by alpha-1-antitrypsin and alpha-2-macroglobulin.

The experimental three-dimensional structure of human APC has been determined to 2.8 Å resolution and reported by Mather et al., EMBO J. 1996; 15; 6822–6831. They report the X-ray structure of APC in a Gla-domainless form. The structure includes a covalently bound inhibitor (D-Phe-Pro-Arg chloromethylketone, PPACK).

Protein C is currently isolated from prothrombin concentrates produced by monoclonal antibody affinity chromatography. Furthermore, protein C is produced recombinantly by expression from mammalian cells or modified protein C.

APC is used for the treatment of genetic and acquired protein C deficiency and is suggested to be used as anticoagulant in patients with some forms of Lupus, following stroke or myocardial infarction, after venous thrombosis, disseminated intravascular coagulation (DIC), septic shock, emboli such as pulmonary emboli, transplantation, such as bone marrow trans-plantation, burns, pregnancy, major surgery/traum and adult respiratory stress syndrome (ARDS).

Recombinant APC is produced by Eli Lilly and Co and phase III trials for the treatment of sepsis (Bernard et al., N Engl J Med (2001), 344, pp. 699–709) has recently been completed. Patients suffering from severe sepsis were given doses of 24 µg/kg/h for a total duration of 96 hours as infusion.

However, relatively high doses and frequent administration is necessary to reach and sustain the desired therapeutic or prophylactic effects of APC due to its short half-life. As a consequence adequate dose regulation is difficult to obtain and the need of frequent intravenous administrations of high levels of APC is problematic and expensive.

A molecule with a longer circulation half-life would decrease the number of necessary administrations and potentially provide more optimal therapeutic APC levels with concomitant enhanced therapeutic effect.

The circulation half-life of APC may be increased, e.g. as a consequence of reduced renal clearance, of reduced proteolytic degradation or reduced inhibition. This may be achieved, e.g., by conjugation APC to a non-polypeptide moiety, e.g. PEG or carbohydrates, capable of conferring a reduced renal clearance to the protein and/or effectively blocking proteolytic enzymes or inhibitors from physical contact with the protein. Furthermore, this may also be achieved by mutating the protein C molecule in such a way that it remains active but blocks the binding of inhibitors to the protein.

PEGylated wild-type APC is described in JP 8-92294.

WO 91/09960 discloses a hybrid protein comprising modifications in the heavy chain part of protein C.

WO 01/59084 describes protein C variants comprising the substitutions D167F+D172K in combination with at least one further substitution in position 10, 11, 12, 32, 194, 195, 228, 149, 254, 302 or 316. The variants disclosed in WO 01/59084 are stated to have an increased anticoagulant activity.

WO 98/44000 broadly describes protein C variants with an increased amidolytic activity.

EP 0 323 149 describes zymogen forms of protein C with the following mutations in the heavy chain: D167F/G/Y/W. Such variants are stated to have an increased sensitivity to activation by thrombin.

WO 00/66754 reported that substitution of the residues naturally occurring in the positions 194, 195, 228, 249, 254, 302 or 316 lead to an increased half-life of APC in human blood as compared to the wild-type APC. The variants disclosed in WO 00/66754 are not within the scope of the present invention.

WO 99/63070 describes a C-terminally truncated form of protein C.

EP 0 946 715 reported chimeric protein C polypeptides where the protein C Gla domain was replaced by Gla domains from other vitamin K-dependent polypeptides, such as factor VII, factor X and prothrombin.

WO 99/20767 and WO 00/66753 discloses vitamin K-dependent polypeptide variants containing modifications in the Gla domain.

U.S. Pat. No. 5,453,373 discloses human protein C derivatives which have altered glycosylation patterns and altered activation regions, such as N313Q and N329Q. The variants disclosed in U.S. Pat. No. 5,453,373 are not within the scope of the present invention.

U.S. Pat. No. 5,460,953 discloses DNA sequences encoding zymogen forms of protein C, which have been engineered so that one or more of the naturally occurring glycosylation sites have been removed. More specifically, U.S. Pat. No. 5,460,953 discloses the variants N97Q, N248Q, N313Q and N329Q. The variants disclosed in U.S. Pat. No. 5,460,953 are not within the scope of the present invention. None of the disclosed variants in any of the above-mentioned prior art references are within the scope of the present invention.

U.S. Pat. No. 5,270,178 is directed to specific protein C variants, wherein I 171 is deleted and wherein Asp is replaced by Asn.

U.S. Pat. No. 5,041,376 relates to a method for identifying and shielding functional sites or epitopes of transportable proteins, wherein additional N-linked glycosylation site(s) have been introduced.

U.S. Pat. No. 5,766,921 is directed to protein C variants having increased resistance to inactivation by human plasma or $\alpha_1$-antitrypsin, where the heavy chain contains substitutions from the corresponding bovine heavy chain.

WO 01/57193 reports a protein C variant comprising a double mutation, one mutation in positions 10, 11, 32 or 33 and one mutation in positions 194, 195, 228, 249, 254, 392 or 316.

WO 01/36462 relates to protein C variants comprising a substitution in position 12, optionally combined with substitutions in positions 10 and/or 11.

WO 00/26354 is directed to a method for producing glycosylated protein variants having reduced allergenicity.

WO 00/26230 is directed to a method for selecting a protein variant having reduced immunogenicity.

The DNA sequence and the corresponding amino acid sequence of human wild-type protein C, including the precursor form thereof, is disclosed in inter alia U.S. Pat. No. 4,775,624 and U.S. Pat. No. 4,968,626.

None of the variants disclosed in any of the above-identified patents/patent applications are within the scope of the present invention.

BRIEF DISCLOSURE OF THE INVENTION

The present invention relates to novel conjugates between polypeptide variants of protein C and a non-polypeptide moiety, to means and methods for preparing such conjugates, to pharmaceutical compositions comprising such conjugates and the use of such conjugates in therapy, in particular for the treatment of a variety of coagulation disorders. The present invention also relates to the polypeptide part of the conjugates of the invention.

Accordingly, in its first aspect the invention relates to a conjugate comprising at least one non-polypeptide moiety covalently attached to a protein C polypeptide that comprises an amino acid sequence which differs from that of a parent protein C polypeptide in at least one introduced and/or at least one removed amino acid residue comprising an attachment group for said non-polypeptide moiety.

In a further aspect the invention relates to a variant of a parent protein C polypeptide, said variant comprising a substitution in a position selected from the group consisting of D172, D189, S190, K191, K192, K193, D214, E215, S216, K217, K218, L220, V243, V245,V250, K251, S252, T253, T254, D255, L296, Y302, H303, S304, S305, R306, E307, K308, E309, A310, R312, T315, F316, V334, S336, N337, M338, I348, L349, D351, R352, E357, E382, G383, L386, L387 and H388, with the proviso that the substitution is not selected from the group consisting of T254S, T254A, T254H, T254K, T254R, T254N, T254D, T254E, T254G, T254Q, Y302S, Y302A, Y302T, Y302H, Y302K, Y302R, Y302N, Y302D, Y302E, Y302G, Y302Q, F316S, F316A, F316T, F316H, F316K, F316R, F316N, F316D, F316E, F316G and F316Q.

In an even further aspect, the present invention relates to the polypeptide part of the conjugate of the invention.

In still further aspects the present invention relates to a nucleotide sequence encoding the polypeptide part of the conjugate of the invention, to a nucleotide sequence encoding the polypeptide variant of the invention, to an expression vector comprising the nucleotide sequence of the invention and to a host cell comprising the nucleotide sequence of the invention or comprising the expression vector of the invention.

Still other aspects of the present invention relates to a pharmaceutical composition comprising the conjugate or the variant of the invention as well as to methods of producing and using the conjugates and variants of the invention.

DETAILED DISCLOSURE OF THE INVENTION

Definitions

In the context of the present application and invention the following definitions apply:

The term "conjugate" (or interchangeably "conjugated polypeptide") is intended to indicate a heterogenous (in the sense of composite or chimeric) molecule formed by the covalent attachment of one or more polypeptides to one or more non-polypeptide moieties such as polymer molecules, lipophilic compounds, sugar moieties or organic derivatizing agents. Preferably, the conjugate is soluble at relevant concentrations and conditions, i.e. soluble in physiological fluids such as blood. Examples of conjugated polypeptides of the invention include glycosylated polypeptides and PEGylated polypeptides.

The term "covalent attachment" or "covalently attached" means that the polypeptide and the non-polypeptide moiety are either directly covalently joined to one another or are indirectly covalently joined to one another through an intervening moiety or moieties such as a bridge, spacer or linkage moiety or moietiers.

The term "non-conjugated polypeptide" may be used about the polypeptide part of the conjugate.

The term "non-polypeptide moiety" is intended to mean a molecule, different from a peptide polymer composed of amino acid monomers and linked together by peptide bonds, which molecule is capable of conjugating to an attachment group of the polypeptide of the invention. Preferred examples of such molecules include polymer molecules, sugar moieties, lipophilic compounds or organic derivatizing agents. When used in the context of a conjugate of the invention it will be understood that the non-polypeptide moiety is linked to the polypeptide part of the conjugate through an attachment group of the polypeptide. As explained above, the non-polypeptide moiety can be directly covalently joined to the attachment group or it can be indirectly covalently joined to the attachment group through an intervening moiety or moieties, such as a bridge spacer or linker moiety or moieties.

The term "polymer molecule" is a molecule formed by covalent linkage of two or more monomers, wherein none of the monomers is an amino acid residue, except where the polymer is human albumin or another abundant plasma protein. The term "polymer" can be used interchangeably with the term "polymer molecule" or "polymeric group".

The term "sugar moiety" is intended to indicate a carbohydrate-containing molecule comprising one or more monosaccharide residues, capable of being attached to the polypeptide (to produce a polypeptide conjugate in the form of a glycosylated polypeptide) by way of in vivo or in vitro glycosylation. The term "in vivo glycosylation" is intended to mean any attachment of a sugar moiety occurring in vivo, i.e. during posttranslational processing in a glycosylating cell used for expression of the polypeptide, e.g. by way of N-linked and O-linked glycosylation. The exact oligosaccharide structure depends, to a large extent, on the glycosylating organism in question. The term "in vitro glycosylation" is intended to refer to a synthetic glycosylation produced in vitro, normally involving covalently linking a sugar moiety to an attachment group of a polypeptide, optionally using a cross-linking agent. In vivo and in vitro glycosylation are discussed in detail further below.

An "N-glycosylation site" has the sequence N-X-S/T/C", wherein X is any amino acid residue except proline, N is asparagine and S/T/C is either serine, threonine or cysteine, preferably serine or threonine, and most preferably threonine. An "O-glycosylation site" is the OH-group of a serine or threonine residue.

The term "attachment group" is intended to indicate a functional group of the polypeptide, in particular of an amino acid residue thereof or a carbohydrate moiety, capable of attaching a non-polypeptide moiety such as a polymer molecule, a sugar moiety, a lipophilic molecule or an organic derivatizing agent. Useful attachment groups and their matching non-polypeptide moieties are apparent from the table below.

| Attachment group | Amino acid | Examples of non-polypeptide moiety | Conjugation method/-Activated PEG | Reference |
| --- | --- | --- | --- | --- |
| —NH$_2$ | N-terminal, Lys | Polymer, e.g. PEG, with amide or imine group | mPEG-SPA Tresylated mPEG | Shearwater Inc. Delgado et al., critical reviews in Therapeutic Drug Carrier Systems 9(3, 4): 249–304 (1992) |

-continued

| Attachment group | Amino acid | Examples of non-polypeptide moiety | Conjugation method/-Activated PEG | Reference |
|---|---|---|---|---|
| —COOH | C-terminal, Asp, Glu | Polymer, e.g. PEG, with ester or amide group. | mPEG-Hz | Shearwater Inc. |
| | | Oligosaccharide moiety | In vitro coupling | |
| —SH | Cys | Polymer, e.g. PEG, with disulfide, maleimide or vinyl sulfone group | PEG-vinylsulphone PEG-maleimide | Shearwater Inc. Delgado et al., critical reviews in Therapeutic Drug Carrier Systems 9(3, 4): 249–304 (1992) |
| | | Oligosaccharide moiety | In vitro coupling | |
| —OH | Ser, Thr, OH—, Lys | Oligosaccharide moiety PEG with ester, ether, carbamate, carbonate | In vivo O-linked glycosylation | |
| —CONH$_2$ | Asn as part of an N-glycosylation site | Oligosaccharide moiety Polymer, e.g. PEG | in vivo N-glycosylation | |
| Aromatic residue | Phe, Tyr, Trp | Oligosaccharide moiety | In vitro coupling | |
| —CONH$_2$ | Gln | Oligosaccharide moiety | In vitro coupling | Yan and Wold, Biochemistry, 1984, Jul 31; 23(16): 3759–65 |
| Aldehyde Ketone | Oxidized oligosaccharide | Polymer, e.g. PEG, PEG-hydrazide | PEGylation | Andresz et al., 1978, Makromol. Chem. 179: 301, WO 92/16555, WO 00/23114 |
| Guanidino | Arg | Oligosaccharide moiety | In vitro coupling | Lundblad and Noyes, Chemical Reagents for Protein Modification, CRC Press Inc., Florida, USA |
| Imidazole ring | His | Oligosaccharide moiety | In vitro coupling | As for guanidine |

For in vivo N-glycosylation, the term "attachment group" is used in an unconventional way to indicate the amino acid residues constituting an N-glycosylation site. Although the asparagine residue of the N-glycosylation site is the one to which the sugar moiety is attached during glycosylation, such attachment cannot be achieved unless the other amino acid residues of the N-glycosylation site are present.

Accordingly, when the non-polypeptide moiety is a sugar moiety and the conjugation is to be achieved by N-glycosylation, the term "amino acid residue comprising an attachment group for the non-polypeptide moiety" as used in connection with alterations of the amino acid sequence of the polypeptide of interest is to be understood as meaning that one or more amino acid residues constituting an N-glycosylation site are to be altered in such a manner that either a functional N-glycosylation site is introduced into the amino acid sequence or removed from said sequence.

Amino acid names and atom names (e.g. CA, CB, CD, CG, SG, NZ, N, O, C, etc.) are used as defined by the Protein DataBank (PDB) (www.pdb.org), which is based on the IUPAC nomenclature (IUPAC Nomenclature and Symbolism for Amino Acids and Peptides (residue names, atom names, etc.), Eur. J. Biochem., 138, 9–37 (1984) together with their corrections in Eur. J. Biochem., 152, 1 (1985)).

The term "amino acid residue" is intended to indicate an amino acid residue contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W) and tyrosine (Tyr or Y) residues.

The terminology used for identifying amino acid positions/substitutions is illustrated as follows: K174 in a given amino acid sequence indicates that position number 174 is occupied by a lysine residue in the amino acid sequence shown in SEQ ID NO:2 or 4. K174S indicates that the lysine residue of position 174 is substituted with a serine residue. Alternative substitutions are indicated with a "/", e.g., K174S/T means that the lysine residue of position 174 is substituted with either a serine residue or a threonine residue. Multiple substitutions are indicated with a "+", e.g., D172N+K174S means that the aspartic acid residue of position 172 is substituted with an asparagine residue and that the lysine residue in position 174 is substituted with a serine residue. The insertion of an additional amino acid residue is indicated in the following way: Insertion of an alanine residue after K174 is indicated by K174KA. A deletion of an amino acid residue is indicated by an asterix. For example, deletion of the lysine residue of position 174 is indicated by K174*. Unless otherwise indicated, the numbering of amino acid residues made herein is made relative to the amino acid sequence of SEQ ID NO:2 or 4.

The term "differs" or "differs from" when used in connection with specific mutations is intended to allow for additional differences being present apart from the specified amino acid difference. For instance, in addition to the removal and/or introduction of amino acid residues comprising an attachment group for the non-polypeptide moiety the protein C polypeptide can comprise other substitutions, insertions or deletions, which are not related to the introduction/removal of such amino acid residues. Thus, in addition to the amino acid alterations disclosed herein aimed at removing and/or introducing attachment sites for the non-polypeptide moiety, it will be understood that the amino acid sequence of the polypeptide conjugate of the invention may, if desired, contain other alterations that need not be related to introduction or removal of attachment sites, i.e. other substitutions, insertions or deletions. These may, for example, include truncation of the N- and/or C-terminus by one or more amino acid residues, or addition of one or more extra residues at the N- and/or C-terminus, e.g. addition of a methionine residue at the N-terminus as well as "conservative amino acid substitutions", i.e. substitutions performed within groups of amino acids with similar characteristics, e.g. small amino acids, acidic amino acids, polar amino acids, basic amino acids, hydrophobic amino acids and aromatic amino acids.

Examples of conservative substitutions in the present invention may in particular be selected from the groups listed in the table below.

| 1 | Alanine (A) | Glycine (G) | Serine (S) | Threonine (T) |
|---|---|---|---|---|
| 2 | Aspartic acid (D) | Glutamic acid (E) | | |
| 3 | Asparagine (N) | Glutamine (Q) | | |
| 4 | Arginine (R) | Histidine (H) | Lysine (K) | |
| 5 | Isoleucine (I) | Leucine (L) | Methionine (M) | Valine (V) |
| 6 | Phenylalanine (F) | Tyrosine (Y) | Tryptophan (W) | |

When used in the present context the term "precursor protein C" refers to the DNA-encoded form of protein C, i.e. it includes the signal peptide (residue −42 to −1), the light chain (residue 1–155), the Lys-Arg dipeptide (residue 156–157) and the heavy chain (158–419), including the activation peptide (residue 158–169), shown in SEQ ID NO:2.

The term "two-chain zymogen protein C" refers to the secreted, inactive form of protein C, which includes the light chain (residue 1–155) and the heavy chain (158–419), including the activation peptide (158–169), shown in SEQ ID NO:4.

The term "one-chain zymogen protein C" refers to the inactive form of protein C, which includes the light chain (residue 1–155), the heavy chain (158–419), including the activation peptide (158–169), and the Lys-Arg dipeptide (residue 156–157) shown in SEQ ID NO:4.

Whenever the term "zymogen protein C" is used this term refers to both the one-chain form and the two-chain form of the zymogen protein C.

The terms "activated protein C", "activated human protein C", "APC" or "human APC" are used about the activated zymogen and includes the light chain (residue 1–155) and the heavy chain (without the activation peptide) of SEQ ID NO:4. The latter amino acid sequence, i.e. the amino acid sequence of activated protein C is sometimes referred to herein as "the APC part of the amino acid sequence shown in SEQ ID NO:4".

The term "protein C" encompasses all of the above-mentioned forms of protein C, i.e. the "precursor protein C" form, the "zymogen protein C" form (the one-chain form as well as the two-chain form) and the "activated protein C form".

The term "parent" is intended to indicate the molecule to be improved in accordance with the present invention. Although the parent polypeptide to be modified by the present invention may be any protein C polypeptide, and thus be derived from any origin, e.g. a non-human mammalian origin, it is preferred that the parent polypeptide is human protein C (i.e. human precursor protein C, human zymogen protein C or human activated protein C) or a fragment or variant thereof.

A fragment is a part of the full-length human protein C sequence, e.g. a C-terminally or N-terminally truncated version thereof. Specific examples of parent protein C polypeptide fragments include human protein C terminally truncated with 1–15 amino acid residues and/or N-terminally truncated with 1–3 amino acid residues.

As mentioned above, the parent protein C polypeptide may also be a variant of human protein C. Specific examples of variants of human protein C includes e.g. addition of a methionine residue at the N-terminus as well as variants containing one or more conservative amino acid substitutions as discussed above. Other examples of variants include human protein C variants wherein one or more amino acids in the protein C Gla domain has been substituted or wherein the entire protein C Gla domain has been substituted with another Gla domain, e.g. the Gla domain of protein S.

The term "variant" (of a parent polypeptide) is intended to cover a polypeptide, which differs in one or more amino acid residues from its parent polypeptide, normally in 1–15 amino acid residues (such as in 1, 2, 3, 4, 5, 6, 7, 8, 9, 10, 11, 12, 13, 14 or 15 amino acid residues), e.g. in 1–10 amino acid residues or in 1–5 amino acid residues.

The term "mutation" and "substitution" are used interchangeably herein.

The term "nucleotide sequence" is intended to indicate a consecutive stretch of two or more nucleotide molecules. The nucleotide sequence may be of genomic, cDNA, RNA, semisynthetic or synthetic origin, or any combination thereof.

The term "polymerase chain reaction" or "PCR" generally refers to a method for amplification of a desired nucleotide sequence in vitro as described, for example, in U.S. Pat. No. 4,683,195. In general, the PCR method involves repeated cycles of primer extension synthesis, using oligonucleotide primers capable of hybridising preferentially to a template nucleic acid.

"Cell", "host cell", "cell line" and "cell culture" are used interchangeably herein and all such terms should be understood to include progeny resulting from growth or culturing of a cell.

"Transformation" and "transfection" are used interchangeably to refer to the process of introducing DNA into a cell.

"Operably linked" refers to the covalent joining of two or more nucleotide sequences, by means of enzymatic ligation or otherwise, in a configuration relative to one another such that the normal function of the sequences can be performed. For example, the nucleotide sequence encoding a presequence or secretory leader is operably linked to a nucleotide sequence coding for a polypeptide if it is expressed as a preprotein that participates in the secretion of the polypeptide: a promoter or enhancer is operably linked to a coding sequence if it affects the transcription of the sequence; a ribosome binding site is operably linked to a coding sequence if it is positioned so as to facilitate translation. Generally, "operably linked" means that the nucleotide sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

The term "introduce" is primarily intended to mean substitution of an existing amino acid residue, but may also mean insertion of an additional amino acid residue.

The term "remove" is primarily intended to mean substitution of the amino acid residue to be removed by another amino acid residue, but may also mean deletion (without substitution) of the amino acid residue to be removed.

The term "functional in vivo half-life" is used in its normal meaning, i.e. the time at which 50% of the biological activity of the polypeptide or conjugate is still present in the body/target organ, or the time at which the activity of the polypeptide or conjugate is 50% of the initial value. As an alternative to determining functional in vivo half-life, "serum half-life" may be determined, i.e. the time at which 50% of the polypeptide or conjugate molecules circulate in the plasma or bloodstream prior to being cleared. Determination of serum half-life is often more simple than determining the functional in vivo half-life and the magnitude of serum half-life is usually a good indication of the magnitude of functional in vivo half-life. Alternatively terms to serum half-life include "plasma half-life", "circulating half-life", "serum clearance", "plasma clearance" and "clearance half-life". The polypeptide or conjugate is cleared by the action of one or more of the reticuloendothelial systems (RES), kidney, spleen or liver, by tissue factor, SEC receptor or other receptor mediated elimination, or by specific or unspecific proteolysis. Normally, clearance depends on size (relative to the cutoff for glomerular filtration), charge, attached carbohydrate chains, and the presence of cellular receptors for the protein. The functionality to be retained is normally selected from anticoagulant, amidolytic or receptor binding activity. The functional in vivo half-life and the serum half-life may be determined by any suitable method known in the art.

The term "increased" as used about the functional in vivo half-life or serum half-life is used to indicate that the relevant half-life of the conjugate or polypeptide is statistically significantly increased relative to that of a reference molecule, e.g. APC, determined under comparable conditions. Normally, functional in vivo or serum half-life is increased when clearance, proteolytic degradation and/or inhibition of the polypeptide is decreased. Thus, preferred conjugates are such conjugates, which, in their activated form, has an increased functional in vivo half-life or an increased serum half-life as compared to human APC. Particular preferred conjugates are such conjugates where the ratio between the serum half-life (or functional in vivo half-life) of said conjugate and the serum half-life (or functional in vivo half-life) of human APC is at least 1.25, more preferably at least 1.50, such as at least 1.75, e.g. at least 2, even more preferably at least 3, such as at least 4, e.g. at least 5, most preferably at least 6, such as at least 7, e.g. at least 8, at least 9 or at least 10.

Clearance mechanisms of relevance for a polypeptide or conjugate of the invention may include one or more of the reticuloendothelial systems (RES), kidney, spleen or liver, receptor-mediated degradation, or specific or non-specific proteolysis. The term "renal clearance" is used in its normal meaning to indicate any clearance taking place by the kidneys, e.g. by glomerular filtration, tubular excretion or tubular elimination. Normally, renal clearance depends on physical characteristics of the conjugate, including molecular weight, size (relative to the cutoff for glomerular filtration), symmetry, shape/rigidity and charge. A molecular weight of about 67 kDa is normally considered to be a cut-off-value for renal clearance. Renal clearance may be measured by any suitable assay, e.g. an established in vivo assay. For instance, renal clearance may be determined by administering a labelled (e.g. radiolabelled or fluorescence labelled) polypeptide conjugate to a patient and measuring the label activity in urine collected from the patient. Reduced renal clearance is determined relative to the reference molecule, such as APC.

The term "activity", "APC activity" or "activated protein C activity" is intended to indicate that the conjugate of the invention, in its activated form, retain the essential properties of APC.

A suitable in vitro APC activity assay (entitled "APC Amidolytic Assay") is described in Example 9 herein. Thus, more particularly, a conjugate of the present invention is classified as having "APC activity" if the conjugate, in its activated form, has an activity of at least 10% of the human APC activity when tested in the "APC Amidolytic Assay" described in Example 9 herein. Preferably, the conjugate has an activity of at least 20% of the human APC activity, such as an activity of at least 30% of the human APC activity, more preferably the conjugate has an activity of at least 40% of the human APC activity, such as an activity of at least 50% of the human APC activity, even more preferably the conjugate has an activity of at least 60% of the human APC activity, e.g. an activity of at least 70% of the human APC activity, most preferably the conjugate has an activity of at least 80% of the human APC activity, such as an activity of at least 90% of the human APC activity. In a very interesting embodiment, the conjugate has an activity, when tested in the "APC Amidolytic Assay" described in Example 9 herein, which is essentially the same or higher than the activity of human APC. It will be understood that the conjugate of the invention and the wild-type human APC should be assayed under identical conditions, i.e. the concentration of both proteins should be identical when assayed as described in Example 9 herein.

Alternatively, the "APC activity" may be measured in the in vitro assay entitled "APC Clotting Assay" described in Example 10 herein. More particularly, a conjugate of the present invention is classified as having "APC activity" if the conjugate, in its activated form, has an anticoagulant activity of at least 5% of the human APC anticoagulant activity when tested in the "APC Clotting Assay" described in Example 10 herein. Preferably, the conjugate has an anticoagulant activity of at least 10% of the human APC anticoagulant activity, such as an anticoagulant activity of at least 20% of the human APC anticoagulant activity, e.g. an anticoagulant activity of at least 30%, more preferably the conjugate has an anticoagulant activity of at least 40% of the human APC anticoagulant activity, such as an anticoagulant activity of at least 50% of the human APC anticoagulant activity, even more preferably the conjugate has an anticoagulant activity of at least 60% of the human APC anticoagulant activity, e.g. an anticoagulant activity of at least 70% of the human APC anticoagulant activity, most preferably the conjugate has an anticoagulant activity of at least 80% of the human APC anticoagulant activity, such as an anticoagulant activity of at least 90% of the human APC anticoagulant activity. In a very interesting embodiment, the conjugate has an anticoagulant activity, when tested in the "APC Clotting Assay" described in Example 10 herein, which is essentially the same or higher than the anticoagulant activity of human APC. Examples of typical PC activity intervals are, for example 5–75% of the human APC anticoagulant activity, such as 10–50% of the human APC anticoagulant activity, such as 10–40% of the human APC anticoagulant activity. It will be understood that the conjugate of the invention and the wild-type human APC should be assayed under identical conditions, i.e. the concentration of both proteins should be identical when assayed as described in Example 10 herein.

The terms "increased resistance towards inactivation by alpha-1-antitrypsin" and "increased resistance towards inactivation by human plasma", respectively, are primarily intended to mean a conjugate of the invention which is inhibited by alpha-1-antitrypsin or human plasma, respectively, to a lesser degree than human APC. In order to enable the skilled person, at an early stage of his development work, to select effective and preferred conjugates, the present inventors have developed suitable preliminary tests, which can easily be carried out by the skilled person in order to initially assess the performance of the conjugate in question. Thus, the "Alpha-1-Antitrypsin Inactivation Assay" (described in Example 11 herein), the "Human Plasma Inactivation Assay I" (described in Example 12 herein) and the "Human Plasma Inactivation Assay II" (described in Example 13 herein) may be employed to initially assess the potential of a selected conjugate. Using either the first, the second, the third or all of these tests, the suitability of a selected conjugate to resist inactivation by either alpha-1-antitrypsin and/or human plasma can be assessed, the rationale being that if a conjugate is strongly inhibited by either alpha-1-antitrypsin or human plasma, or both, it is normally not necessary to carry out further test experiments.

Therefore, a conjugate, which is particular interesting for the purposes described herein, is a conjugate which, in its activated form, has a residual activity of at least 20% when tested in the "Alpha-1-Antitrypsin Inactivation Assay" described in Example 11 herein using an inhibitor concentration of 16.6 µM. Preferably, the conjugate has a residual activity of at least 30%, such as a residual activity of at least 40%, more preferably the conjugate has a residual activity of at least 50%, such as a residual activity of at least 60%, even more preferably the conjugate has a residual activity of at least 70%, such as a residual activity at least 75%, most preferably the conjugate has a residual activity of at least 80%, such as at least 85%.

Alternatively, or in addition to the above-mentioned test, the suitability of a selected conjugate may be tested in the "Human Plasma Inactivation Assay I". Thus, a conjugate which is particular interesting for the purposes described herein, is a conjugate which, in its activated form, has a residual activity of at least 20% when tested in the "Human Plasma Inactivation Assay I" described in Example 12 herein. Preferably, the conjugate has a residual activity of at least 30%, such as a residual activity of at least 40%, more preferably the conjugate has a residual activity of at least 50%, such as a residual activity of at least 60%, even more preferably the conjugate has a residual activity of at least 70%, such as a residual activity at least 75%.

Alternatively, or in addition to the above-mentioned test(s), the suitability of a selected conjugate may be tested in the "Human Plasma Inactivation Assay II". Thus, a conjugate which is particular interesting for the purposes described herein, is a conjugate where the ratio between the in vitro half-life of said conjugate, in its activated form, and the in vitro half-life of human APC is at least 1.25 when tested in the "Human Plasma Inactivation Assay II" described in Example 13 herein, preferably at least 1.5, such as at least 2, more preferably at least 3, such as at least 4, even more preferably at least 5, such as at least 6, most preferably at least 7, such as at least 8, in particular at least 9, such as at least 10.

The term "reduced immunogenicity" is intended to indicate that the conjugate gives rise to a measurably lower immune response than a reference molecule, e.g. wild-type human APC or wild-type human protein C, as determined under comparable conditions. The immune response may be a cell or antibody mediated response (see, e.g., Roitt: Essential Immunology (8th Edition, Blackwell) for further definition of immunogenicity). Normally, reduced antibody reactivity is an indication of reduced immunogenicity. Reduced immunogenicity may be determined by use of any suitable method known in the art, e.g. in vivo or in vitro.

The term "anti-inflammatory effect" is intended to mean that the conjugates of the invention prevent induction of various pro-inflammatory cytokines and adhesion molecules, such as tumor necrosis factor alpha, interleukin-1,-8 and E-selecting, either in vitro or in vivo.

Whether a conjugate possesses an anti-inflammatory effect may easily be assessed by the skilled person using the "APC Anti-inflammatory Assay" disclosed in Example 14 herein or other similar assasys.

The terms "at least 25% of its side chain exposed to the surface" and "at least 50% of its side chain exposed to the surface" are defined with reference to Example 1, where the calculations, etc. are described in detail.

Conjugate of the Invention

The conjugates of the present invention are the result of a generally new strategy for developing improved protein C molecules. More specifically, by removing and/or introducing an amino acid residue comprising an attachment group for the non-polypeptide moiety it is possible to specifically adapt the polypeptide so as to make the molecule more susceptible to conjugation to the non-polypeptide moiety of choice, to optimize the conjugation pattern, e.g. to ensure an optimal distribution and number of non-polypeptide moieties on the surface of the protein C molecule and to ensure that only the attachment groups intended to be conjugated is present in the molecule, and thereby obtain a new conjugate molecule, which has APC activity and in addition one or more improved properties as compared to protein C molecules available today. For instance, when the total number of amino acid residues comprising an attachment group for the non-polypeptide of choice is increased or decreased to an optimized level, the renal clearance of the conjugate is typically significantly reduced due to the altered shape, size and/or charge of the molecule achieved by the conjugation. Furthermore, we have found that it is possible to design the attachment of a non-polypeptide moiety to an attachment group in the polypeptide part of the conjugate so that inactivation by human plasma or certain inhibitors, such as alpha-1-antitrypsin, is significantly reduced (see below).

The amino acid residue comprising an attachment group for a non-polypeptide moiety, either it be removed or introduced, is selected on the basis of the nature of the non-polypeptide moiety of choice and, in most instances, on the basis of the method in which conjugation between the polypeptide and the non-polypeptide moiety is to be achieved. For instance, when the non-polypeptide moiety is a polymer molecule such as a polyethylene glycol or polyalkylene oxide derived molecule amino acid residues comprising an attachment group may be selected from the group consisting of lysine, cysteine, aspartic acid, glutamic acid, histidine, and tyrosine, preferably cysteine and lysine, in particular lysine. When the non-polypeptide moiety is a sugar moiety the attachment group is, e.g., an in vivo glycosylation site, preferably an N-glycosylation site.

Whenever an attachment group for a non-polypeptide moiety is to be introduced into or removed from the protein C polypeptide in accordance with the present invention, the position of the polypeptide to be modified is conveniently selected as follows:

The position is preferably located at the surface of the protein C polypeptide, and more preferably occupied by an amino acid residue having more than 25% of its side chain exposed to the surface, such as more than 50% of its side chain exposed to the surface. Such positions have been identified on the basis of an analysis of a 3D structure of the human wild-type APC molecule as described in the Methods section herein. Furthermore, homologous positions in non-human APC polypeptides (including variants thereof) comprising an amino acid sequence being homologous to that of wild-type human protein C may easily be determined by suitable alignment of the respective sequences or 3D structures.

In order to determine an optimal distribution of attachment groups, the distance between amino acid residues located at the surface of the polypeptide is calculated on the basis of a 3D structure of the polypeptide. More specifically, the distance between the CB's of the amino acid residues comprising such attachment groups, or the distance between the functional group (NZ for lysine, CG for aspartic acid, CD for glutamic acid, SG for cysteine) of one and the CB of another amino acid residue comprising an attachment group are determined. In case of glycine, CA is used instead of CB. In the polypeptide part of a conjugate of the invention, any of said distances is preferably more than 8 Å, in particular more than 10 Å in order to avoid or reduce heterogeneous conjugation.

The total number of amino acid residues to be altered in accordance with the present invention, e.g. as described in the subsequent sections herein, (as compared to the parent protein C molecule) will typically not exceed 15. The exact number of amino acid residues and the type of amino acid residues to be introduced depends, inter alia, on the desired nature and degree of conjugation (e.g. the identity of the non-polypeptide moiety, how many non-polypeptide moieties it is desirable or possible to conjugate to the polypeptide, where in the polypeptide conjugation should be performed or avoided, etc.). Preferably, the polypeptide part of the conjugate of the invention or the polypeptide of the invention comprises an amino acid sequence which differs in 1–15 amino acid residues from the amino acid sequence shown in SEQ ID NO:4, such as in 1–8 or 2–8 amino acid residues, e.g. in 1–5 or 2–5 amino acid residues. Thus, normally the polypeptide part of the conjugate or the polypeptide of the invention comprises an amino acid sequence which differs from the amino acid sequence shown in SEQ ID NO:4 in 1, 2, 3, 4, 5, 6, 7, 8, 9, 10, 11, 12, 13, 14 or 15 amino acid residues.

Preferably, the conjugate of the invention has one or more improved properties as compared to wild-type human APC, including increased functional in vivo half-life, increased serum half-life, increased resistance to inhibitors, reduced renal clearance, reduced immunogenicity and/or increased bioavailability. It is contemplated that a conjugate of the present invention offers a number of advantages over the currently available APC products, including longer duration between injections, administration of less protein, and fewer side effects.

Furthermore, a reduced anticoagulant activity might be beneficial for reducing the risk of bleeding while maintaining the anti-inflammatory effect of the APC conjugates. This might be especially important when the conjugate has an extended plasma half-life. These new properties should enhance the anti-inflammatory effect compared to the anticoagulant activity allowing a more effective and safe treatment.

Typically, the conjugate according to the invention has a molecular weight of at least about 67 kDa, preferably at least about 70 kDa, although a lower molecular weight may also give rise to a reduced renal clearance. Polymer molecules, such as PEG, or introduced glycosylation sites have been found to be particularly useful for adjusting the molecular weight of the conjugate.

The conjugate of the invention comprises a sufficient number or type of non-polypeptide moieties to improve one or more of the above mentioned desired properties of the protein C polypeptide. Normally a conjugate of the invention comprises 1–10 first non-polypeptide moieties, in particular 1–8 or 1–5 first non-polypeptide moieties.

The conjugate of the invention may further comprise at least one second non-polypeptide moiety which is different from said first non-polypeptide moiety. For instance, the conjugate of the invention may comprise 1–10 second non-polypeptide moieties, in particular 1–8 or 1–5 second non-polypeptide moieties. For instance, when the first non-polypeptide moiety is a sugar moiety, in particular an in vivo attached sugar moiety, a second non-polypeptide moiety of interest could be a polymer of the PEG type. The in vivo attached sugar moiety may be attached to a naturally occurring in vivo glycosylation site of the polypeptide, or an introduced site.

In a very interesting embodiment of the invention the non-polypeptide moiety is introduced in the active site region of protein C, the rationale being that introduction of a non-polypeptide moiety or moieties in this particular region of the protein C molecule will impair binding of inhibitors (such as alpha-1-antitrypin) to APC while still retaining a substantial APC activity. This, in turn, has the consequence that such conjugates will exhibit a significantly prolonged half-life compared to wild-type human APC since elimination of the inhibitor/APC complex via hepatic receptors is avoided or at least reduced. Selection of amino acid residues, which are located in the active site region of protein C is described in detail in Example 2 herein.

When used herein the term "active site region" is defined with reference to Example 2 herein, where the actual amino acid residues which constitute the active site region are shown.

In a particular preferred embodiment of the invention, an attachment group for a non-polypeptide moiety is introduced in a position of the active site region which is occupied by an amino acid residue having at least 25% of its side chain exposed to the surface (see Example 3 herein), i.e. an attachment group for a non-polypeptide moiety is introduced in a position selected from the group consisting of D172, D189, S190, K191, K192, K193, D214, E215, S216, K217, K218, L220, V243, V245, N248, S250, K251, S252, T253, T254, D255, L296, Y302, H303, S304, S305, R306, E307, K308, E309, A310, K311, R312, N313, R314, T315, F316, V334, S336, N337, M338, I348, L349, D351, R352, E357, E382, G383, L386, L387, and H388, (H211 and C384 being excluded). Preferably, the introduced attachment group is an attachment group for a sugar moiety, in particular an in vivo N-glycosylation site (see the section entitled Conjugate of the invention where the non-polypeptide moiety is a sugar moiety).

Conjugate of the Invention where the Non-Polypeptide Moiety is a Sugar Moiety

As explained above, in a preferred embodiment the present invention relates to a conjugate comprising at least one introduced glycosylation site, in particular an in vivo N-glycosylation site, covalently attached to a protein C polypeptide that comprises an amino acid sequence which differs from a parent protein C polypeptide, in particular from the amino acid sequence shown in SEQ ID NO:4 or a variant thereof, in at least one introduced glycosylation site.

Preferably, the glycosylation site is introduced in a position, which is occupied by an amino acid residue having at least 25% of its side chain exposed to the surface, such as at least 50% of its side chain exposed to the surface. Such amino acid residues are identified in Example 1 herein. It should be understood that when the term "at least 25% (or at least 50%) of its side chain exposed to the surface" is used in connection with introduction of an in vivo N-glycosylation site this term refers to the surface accessibility of the amino acid side chain in the position where the sugar moiety is actually attached. In many cases it will be necessary to introduce a serine or a threonine residue in position +2 relative to the asparagine residue to which the sugar moiety is actually attached (unless, of course, this position is already occupied by a serine or a threonine residue) and these positions, where the serine or threonine residues are introduced, are allowed to be buried, i.e. to have less than 25% of their side chains exposed to the surface.

In order to impair the binding of inhibitors, such as alpha-1-antitrypsin, to APC the glycosylation site is preferably introduced in a position which is within the active site region (defined in Example 2 herein) and which is occupied by an amino acid residue having at least 25% of its side chain exposed to the surface (defined in Example 3 herein), i.e. the introduced in vivo N-glycosylation site is preferably selected from the group consisting of D172N+K174S, D172N+K174T, D189N+K191S, D189N+K191 T, S190N+K192S, S190N+K192T, K191N+K193S, K191N+K193T, K192N+L194S, K192N+L194T, K193N+A195S, K193N+A195T, D214N, D214N+S216T, E215N+K217S, E215N+K217T, S216N+K218S, S216N+K218T, K217N+L219S, K217N+L219T, K218N+L220S, K218N+L220T, L220N+R222S, L220N+R222T, V243N+V245S, V243N+V245T, V245N+P247S, V245N+P247T, S250N, S250N+S252T, K251N, K251N+T253S, S252N, S252N+T254S, T253N+D255S, T253N+D255T, T254N+N256S, T254N+N256T, D255N+D257S, D255N+D257T, L296N, L296N+T298S, Y302N, Y302N+S304T, H303N, H303N+S305T, S304N+R306S, S304N+R306T, S305N+E307S, S305N+E307T, R306N+K308S, R306N+K308T, E307N+E309S, E307N+E309T, K308N+A310S, K308N+A310T, E309N+K311S, E309N+K311T, A310N+R312S, A310N+R312T, R312N+R314S, R312N+R314T, T315N+V317S, T315N+V317T, F316N+L318S, F316N+L318T, V334N, V334N+S336T, S336N+M338S, S336N+M338T, V339S, V339T, M338N, M338N+S340T, I348N+G350S, I348N+G350T, L349N+D351S, L349N+D351T, D351N+Q353S, D351N+Q353T, R352N+D354S, R352N+D354T, E357N+D359S, E357N+D359T, G383N+G385S, G383N+G385T, L386N+H388S, L386N+H388T, L387N+N389S, L387N+N389T, H388N+Y390S and H388N+Y390T.

More preferably, the introduced in vivo N-glycosylation site is selected from the group consisting of S190N+K192S, S190N+K192T, K191N+K193S, K191N+K193T, D189N+K191S, D189N+K191T, D214N, D214N+S216T, K217N+L219S, K217N+L219T, K251N, K251N+T253S, S252N, S252N+T254S, T253N+D255S, T253N+D255T, Y302N, Y302N+S304T, S305N+E307S, S305N+E307T, E307N+E309S, E307N+E309T, S336N+M338S, S336N+M338T, V339S, V339T, M338N, M338N+S340T, G383N+G385S, G383N+G385T, L386N+H388S and L386N+H388T.

Even more preferably the introduced in vivo N-glycosylation site is selected from the group consisting of D189N+K191T, K191N+K193T, D214N, K251N, S252N, T253N+D255T, Y302N, S305N+E307T, S336N+M338T, V339T, M338N, G383N+G385T, and most preferably the introduced in vivo N-glycosylation site is selected from the group consisting of D189N+K191T, K191N+K193T, D214N, T253N+D255T, S305N+E307T, S336N+M338T, M338N, G383N+G385T and L386N+H388T. In a particular preferred embodiment the introduced in vivo N-glycosylation site is selected from the group consisting of D189N+K191T, D214N and L386N+H388T.

As explained above, the increased resistance towards inactivation by alpha-1-antitrypsin and/or human plasma may be determined and assessed by the "Alpha-1-Antritrypsin Inactivation Assay", the "Human Plasma Inactivation Assay I" or the "Human Plasma Inactivation Assay II" disclosed herein.

The conjugate of the invention may contain a single in vivo glycosylation site (in addition to the already present glycosylation sites at positions 97, 248, 313 and 329). However, in order to obtain efficient shielding of protease cleavage sites on the surface of the parent polypeptide and/or to efficiently impair inhibitor binding, it is often desirable that the polypeptide part of the conjugate comprises more than one in vivo glycosylation site, in particular 2–5 (additional) in vivo glycosylation sites, such as 2, 3, 4 or 5 (additional) in vivo glycosylation sites, preferably introduced by one or more of the substitutions described in any of the above lists.

Furthermore, the amino acid sequence of a polypeptide having at least one of the above mentioned in vivo N-glycosylation site modifications may differ from that of the parent polypeptide in that at least one cysteine residue has been introduced as identified above in the section entitled "Conjugate of the invention having a non-polypeptide moiety attached to a cysteine residue", or at least one non-cysteine residue has been introduced as identified above in the section entitled "Conjugate of the invention having a non-polypeptide moiety attaching to a non-cysteine residue".

Moreover, the polypeptide part of the conjugate of the invention may contain additional mutations, which are known to be advantageous. For example, in addition to the glycosylation sites discussed above, the polypeptide part of the conjugate may contain a substitution in a position selected from the group consisting of L194, A195, L228, Y249 and combinations thereof, in particular L194S, L194S+T245S and L194A+T254S (see WO 00/66754). Other examples of preferred additional substitutions include substitution or introduction of one or more glycosylation site(s) at or near positions known to be susceptible to proteolytic degradation. One position that is known to be susceptible to proteolytic degradation is H10 of wild-type human APC (see WO 98/48822).

It will be understood that in order to prepare a conjugate according to this aspect of the invention, the polypeptide must be expressed in a glycosylating host cell capable of attaching sugar moieties at the glycosylation sites or alternatively subjected to in vitro glycosylation. Examples of glycosylating host cells are given in the section below entitled "Coupling to a sugar moiety".

Conjugate of the Invention wherein the Non-Polypeptide Moiety is Attached to a Cysteine Residue In another embodiment of the invention, the present invention relates to a conjugate comprising at least one non-polypeptide moiety, in particular a polymer molecule, covalently attached to a protein C polypeptide that comprises an amino acid sequence which differs from a parent protein C polypeptide, in particular from the amino acid sequence shown in SEQ ID NO:4 or a variant thereof, in at least one cysteine residue has been introduced and/or removed, in particular introduced. Thus, in an interesting embodiment of the invention the non-polypeptide moiety has cysteine as an attachment group. Preferably, the cysteine attachment group is introduced in a position which is occupied by an amino acid residue having at least 25% of its side chain exposed to the surface, such as at least 50% of its side chain exposed to the surface. Such amino acid residues are identified in Example 1 herein. Of particular interest among these positions are positions that in the parent polypeptide are occupied by a T or an S residue, preferably an S residue. In accordance herewith, an interesting cysteine-modified conjugate is one, wherein a cysteine residue has been introduced into at least one position selected from the group consisting of S3, S11, S12, T37, S42, S61, T68, S75, S77, S82, S99, S119, S153, S190, S216, S252, T253, T268, S270, S281, S304, S305, T315, S332, S336, S340, S367, and S416, and more preferably from the group consisting of S3, S11, S12, S42, S61, S75, S77, S82, S99, S119, S153, S190, S216, S252, S270, S281, S304, S305, S332, S336, S340, S367, and S416.

In a similar way as described above (see the section entitled "Conjugate of the invention where the non-polypeptide moiety is a sugar moiety" the cysteine residue is preferably introduced in a position which is within the active site region (defined in Example 2 herein) and which is occupied by an amino acid residue having at least 25% of its side chain exposed to the surface (defined in Example 3 herein), i.e. the cysteine residue is preferably introduced in a position selected from the group consisting of D172, D189, S190, K191, K192, K193, D214, E215, S216, K217, K218, L220, V243, V245, S250, K251, S252, T253, T254, D255, L296, Y302, H303, S304, S305, R306, E307, K308, E309, A310, R312, T315, F316, V334, S336, V339, M338, I348, L349, D351, R352, E357, G383, E385, L386, L387 and H388. More preferably, the cysteine residue is introduced in a positions selected from the group consisting of D189, S190, K191, D214, K217, K251, S252, T253, Y302, S305, E307, S336, V339, M338, G383 and L386.

The polypeptide part of the conjugate according to this embodiment typically comprises 1–10 introduced cysteine residues, in particular 1–5 or 1–3 introduced cysteine residues, e.g. 1, 2 or 3 introduced cysteine residues.

While the non-polypeptide moiety of the conjugate according to this aspect of the invention may be any molecule which, when using the given conjugation method has a cysteine residue as an attachment group (such as an polymer moiety, a lipophilic group or an organic derivatizing agent), it is preferred that the non-polypeptide moiety is a polymer molecule, e.g. any of the molecules mentioned in the section entitled "Conjugation to a polymer molecule". Preferably, the polymer molecule is selected from the group consisting of linear or branched polyethylene glycol or polyalkylene oxide. Most preferably, the polymer molecule is PEG, such as VS-PEG. The conjugation between the polypeptide and the polymer may be achieved in any suitable manner, e.g. as described in the section entitled "Conjugation to a polymer molecule", e.g. by using a one step method or by the stepwise manner referred to in said section. When the polypeptide comprises only one conjugatable cysteine residue, this is preferably conjugated to a first non-polypeptide moiety with a molecular weight of at least about 10 kDa or at least about 15 kDa, such as a molecular weight of about 12 kDa, about 15 kDa or about 20 kDa, either directly conjugated or indirectly through a low molecular weight polymer (as disclosed in WO 99/55377). When the conjugate comprises two or more first non-polypeptide moieties, normally each of these has a molecular weight of about 5 kDa, about 10 kDa or about 12 kDa.

The conjugate according to this embodiment may comprise at least one second non-polypeptide moiety, such as 1–10, 1–8, 1–5 or 1–3 such moieties. When the first non-polypeptide moiety is a polyalkylene oxide or PEG derived polymer, the second non-polypeptide moiety is preferably a sugar moiety, in particular an in vivo attached moiety. The sugar moiety may be present at one or more of the naturally-occurring glycosylation sites present in the parent polypeptide, or at an introduced glycosylation site. Suitable introduced glycosylation sites, in particular N-glycosylation sites, are described in the section entitled "Conjugate of the invention wherein the non-polypeptide moiety is a sugar moiety".

Moreover, the polypeptide part of the conjugate of the invention may contain additional mutations, which are known to be advantageous. For example, in addition to the introduced cysteine residues discussed above, the polypeptide part of the conjugate may contain a substitution in a position selected from the group consisting of L194, A195, L228, Y249 and combinations thereof, in particular. L194S, L194S+T245S and L194A+T254S (see WO 00/66754). Other examples of preferred additional substitutions include substitution or introduction of one or more cysteine residue(s) at or near positions known to be susceptible to proteolytic degradation. One position that is known to be susceptible to proteolytic degradation is H10 of wild-type human APC (see WO 98/48822).

Conjugate of the Invention wherein the Non-Polypeptide Moiety is Attached to a Non-Cysteine Moiety Based on the present disclosure the skilled person will be aware that amino acid residues comprising other attachment groups may be introduced by substitution into the parent polypeptide, using the same approach as that illustrated above with glycosylation sites and cysteine residues. For instance, one or more amino acid residues comprising an acid group (glutamic acid or aspartic acid), tyrosine, serine or lysine may be introduced into the positions discussed above (see the sections entitled "Conjugate of the invention where the non-polypeptide moiety is a sugar moiety" and "Conjugate of the invention wherein the non-polypeptide moiety is attached to a cysteine residue").

Conjugate of the Invention having a Reduced Anticoagulant Activity

Studies have been shown that APC interacts with factor Va and VIIIa through the EGF domains collectively with the protease domain (Zhang et al., *Biochemistry* 1994; 33; 823–831). This protein-protein interaction is important for the anticoagulant activity because it promotes the contact between APC and these two cofactors. On the other hand, the interaction between APC and EPCR is predominantly determined by the binding of the Gla domain of APC to EPCR (Esmon et al., *Haematologica* 1999; 84; 363–368). It is also known that the proteolytic activity of APC is important for the anti-inflammatory activity. Therefore, mutations introduced in the EGF domains might only affect the anticoagulant activity of APC without influencing the anti-inflammatory activity. In addition, it is known that serpins binds and inactivates various proteases by binding directly into the catalytic active site. Thus, the inactivation process of APC in circulation by the serpins will not be influenced by these EGF domain mutations and will therefore not affect the plasma half-life of APC.

Thus, in a further aspect the present invention relates to novel variants of parent protein C conjugates, wherein at least one attachment group for a non-polypeptide amino acid residue has been introduced in the EGF-1 and/or the EGF-2 domain and wherein such variants have a decreased anticoagulant activity as compared to human APC and wherein the anti-inflammatory properties have not been substantially changed as compared to human APC.

More particularly, the present invention relates to a conjugate comprising at least one sugar moiety covalently attached to a protein C polypeptide that comprises an amino acid sequence which differs from that of a parent protein C polypeptide in at least one in vivo glycosylation site has been introduced by a substitution selected from the group consisting of H66N, H66N+T68S, 173N, 173N+S75T, S75N, S75N+S77T, D79N+R81S, D79N+R81T, E92N, E92N+S94T, G104N, G104N+T106S, R117N, R117N+S119T, D128N+L130S and D128N+L130T, preferably from the group consisting of H66N, I73N+S75T, S75N+S77T, D79N+R81T, E92N, G104N, R117N+S119T and D128N+L130T.

As explained above such conjugates are believed to exhibit a significantly reduced anticoagulant activity while essentially maintaining the anti-inflammatory effect of human APC.

Thus, in a preferred embodiment, the present invention relates to a conjugate comprising at least one sugar moiety covalently attached to a protein C polypeptide that comprises an amino acid sequence which differs from that of a parent protein C polypeptide in at least one in vivo glycosylation site has been introduced by a substitution selected from the group consisting of H66N, H66N+T68S, 173N, 173N+S75T, S75N, S75N+S77T, D79N+R81S, D79N+R81T, E92N, E92N+S94T, G104N, G104N+T106S, R117N, R117N+S119T, D128N+L130S and D128N+L130T, preferably from the group consisting of H66N, 173N+S75T, S75N+S77T, D79N+R81T, E92N, G104N, R117N+S119T and D128N+L130T, wherein i) the conjugate, in its activated form, has an anticoagulant activity of 0–50% of the human APC anticoagulant activity when tested in the "APC Clotting Assay" described in Example 10 herein, and ii) the ratio between the $IC_{50}$-value for the variant ($IC_{50,variant}$), in its activated form, and the $IC_{50}$-value for the wild-type human APC ($IC_{50,wt}$) is less than or equal to 1.20, when determined in accordance with the "APC Anti-inflammatory Assay" described in Example 14 herein.

In interesting embodiments of the invention the conjugate, in its activated form, has an anticoagulant activity of 10–50% of the human APC anticoagulant activity when tested in the "APC Clotting Assay" described in Example 10 herein, such as an anticoagulant activity of 10–40% of the human APC anticoagulant activity, e.g. 10–30% of the human APC anticoagulant activity.

It is preferred that the anti-inflammatory effect of the conjugate according to this aspect of the invention is retained. As indicated above, the anti-inflammatory effect of the conjugate should not be less than 80% of the anti-inflammatory effect of the human APC (expressed as $IC_{50,variant}/IC_{50,wt} \leqq 1.20$). Preferably, the anti-inflammatory effect of the conjugate, in its activated form is essentially the same as the anti-inflammatory effect of human APC when determined in the in accordance with the "APC Anti-inflammatory Assay" described in Example 14 herein. For example, it is preferred that the ratio between the $IC_{50}$-value for the variant ($IC_{50,variant}$), in its activated form, and the $IC_{50}$-value for the wild-type human APC ($IC_{50,wt}$) is within the following ranges: $0.80 \leqq IC_{50,variant}/IC_{50,wt} \leqq 1.20$, preferably $0.80 \leqq IC_{50,variant}/IC_{50,wt} \leqq 1.10$, e.g. $0.90 \leqq IC_{50,variant}/IC_{50,wt} \leqq 1.10$, or $0.95 \leqq IC_{50,variant}/IC_{50,wt} \leqq 1.05$, in particular $IC_{50,variant}/IC_{50,wt} \approx 1$.

It will be understood that the above-mentioned variants may be combined with the modifications described elsewhere in the present application. In particular, the above-mentioned substitutions may be combined with the modifications described herein which give rise to an increased in vivo half-life.

Thus, an interesting conjugate according to the present invention is a conjugate comprising at least one sugar moiety covalently attached to a protein C polypeptide that comprises an amino acid sequence which differs from that of a parent protein C polypeptide in at least two substitutions have been performed, the first substitution being selected from the group consisting of H66N, H66N+T68S, 173N, I73N+S75T, S75N, S75N+S77T, D79N+R81S, D79N+R81T, E92N, E92N+S94T, G104N, G104N+T106S, R117N, R117N+S119T, D128N+L130S and D128N+L130T, preferably from the group consisting of H66N, 173N+S75T, S75N+S77T, D79N+R81T, E92N, G104N, R117N+S119T and D128N+L130T, the second substitution being selected from the group consisting of D172N+K174S, D172N+K174T, D189N+K191S, D189N+K191T, S190N+K192S, S190N+K192T, K191N+K193S, K191N+K193T, K192N+L194S, K192N+L194T, K193N+A195S, K193N+A195T, D214N, D214N+S216T, E215N+K217S, E215N+K217T, S216N+K218S, S216N+K218T, K217N+L219S, K217N+L219T, K218N+L220S, K218N+L220T, L220N+R222S, L220N+R222T, V243N+V245S, V243N+V245T, V245N+P247S, V245N+P247T, S250N, S250N+S252T, K251N, K251N+T253S, K251D, K251E, S252N, S252N+T254S, T253N+D255S, T253N+D255T, T254N+N256S, T254N+N256T, D255N+D257S, D255N+D257T, L296N, L296N+T298S, Y302N, Y302N+S304T, H303N, H303N+S305T, S304N+R306S, S304N+R306T, S305N+E307S, S305N+E307T, R306N+K308S, R306N+K308T, E307N+E309S, E307N+E309T, K308N+A310S, K308N+A310T, E309N+K311S, E309N+K311T, A310N+R312S, A310N+R312T, R312N+R314S, R312N+R314T, T315N+V317S, T315N+V317T, F316N+L318S, F316N+L318T, V334N, V334N+S336T, S336N+M338S, S336N+M338T, V339S, V339T, M338N, M338N+S340T, 1348N+G350S, 1348N+G350T, L349N+D351S, L349N+D351T, D351N+Q353S, D351N+Q353T, R352N+D354S, R352N+D354T, E357N+D359S, E357N+D359T, G383N+G385S, G383N+G385T, L386N+H388S, L386N+H388T, L387N+N389S, L387N+N389T, H388N+Y390S and H388N+Y390T, preferably from the group consisting of S190N+K192S, S190N+K192T, K191N+K193S, K191N+K193T, D189N+K191S, D189N+K191T, D214N, D214N+S216T, K217N+L219S, K217N+L219T, K251N, K251N+T253S, K251D, K251E, S252N, S252N+T254S, T253N+D255S, T253N+D255T, Y302N, Y302N+S304T, S305N+E307S, S305N+E307T, E307N+E309S, E307N+E309T, S336N+M338S, S336N+M338T, V339S, V339T, M338N, M338N+S340T, G383N+G385S, G383N+G385T, L386N+H388S and L386N+H388T, more preferably from the group consisting of D189N+K191T, K191N+K193T, D214N, K251N, K251D, S252N, T253N+D255T, Y302N, S305N+E307T, S336N+M338T, V339T, M338N, G383N+G385T, even more preferably from the group consisting of D189N+K191T, K191N+K193T, D214N, K251D, T253N+D255T, S305N+E307T, S336N+M338T, M338N, G383N+G385T and L386N+H388T, most preferably from the group consisting of D189N+K191T, D214N. K251D and L386+H388T.

It will be understood that such conjugates, in their activated forms, are contemplated to exhibit an increased in vivo half-life, a reduced anticoagulant activity and an essentially unaltered anti-inflammatory effect when assayed in accordance with the test methods described herein.

In particular, it is preferred that such conjugates, as described immediately above, fulfill the below requirements, namely that i) the conjugate, in its activated form, has an anticoagulant activity of 0–50% of the human APC anticoagulant activity when tested in the "APC Clotting Assay" described in Example 10 herein, and ii) the ratio between the $IC_{50}$-value for the variant ($IC_{50,variant}$), in its activated form, and the $IC_{50}$-value for the wild-type human APC ($IC_{50,wt}$) is less than or equal to 1.20, when determined in accordance with the "APC Anti-inflammatory Assay" described in Example 14 herein, and iii) the conjugate, in its activated form, has a residual activity of at least 20% when tested in the "Alpha-1-Antitrypsin Inactivation Assay" described in Example 11 herein using an inhibitor concentration of 16.6 µM, or the conjugate, in its activated form and when tested in the "Human Plasma Inactivation Assay I" described in Example 12 herein, has a residual activity of at least 20%, or the ratio between the in vitro half-life of said conjugate, in its activated form, and the in vitro half-life of human APC is at least 1.25 when tested in the "Human Plasma Inactivation Assay II" described in Example 13 herein, or the ratio between the functional in vivo half-life or the serum half-life of said conjugate, in its activated form, and the functional in vivo half-life or serum half-life of human APC is at least 1.25.

In an interesting embodiment such a conjugate, in its activated form, has an anticoagulant activity of 10–50% of the human APC anticoagulant activity when tested in the "APC Clotting Assay" described in Example 10 herein, such as an anticoagulant activity of 10–40% of the human APC anticoagulant activity, e.g. 10–30% of the human APC anticoagulant activity.

It is preferred that the anti-inflammatory effect of the conjugate according to this aspect of the invention is retained. As indicated above, the anti-inflammatory effect of the conjugate should not be less than 80% of the anti-inflammatory effect of the human APC (expressed as $IC_{50,variant}/IC_{50,wt} \leq 1.20$). Preferably, the anti-inflammatory effect of the conjugate, in its activated form is essentially the same as the anti-inflammatory effect of human APC when determined in the in accordance with the "APC Anti-inflammatory Assay" described in Example 14 herein. For example, it is preferred that the ratio between the $IC_{50}$-value for the variant ($IC_{50,variant}$), in its activated form, and the $IC_{50}$-value for the wild-type human APC ($IC_{50,wt}$) is within the following ranges: $0.80 \leq IC_{50,variant}/IC_{50,wt} \leq 1.20$, preferably $0.80 \leq IC_{50,variant}/IC_{50,wt} \leq 1.10$, e.g. $0.90 \leq IC_{50,variant}/IC_{50,wt} \leq 1.10$, or $0.95 \leq IC_{50,variant}/IC_{50,wt} \leq 1.05$, in particular $IC_{50,variant}/IC_{50,wt} \approx 1$.

Moreover, it is preferred that the conjugate fulfills the above-mentioned criteria for inactivation and/or half-life in the "Alpha-1-Antitrypsin Inactivation Assay", "Human Plasma Inactivation Assay I", "Human Plasma Inactivation Assay II", the functional in vivo half-life or the serum half-life, at the levels mentioned in the section entitled "definitions".

Polypeptide Variants of the Invention

In a further aspect the present invention relates to generally novel variants of parent protein C polypeptides. The novel variants are important intermediate compounds for the preparation of conjugates of the invention. In addition, and as will be apparent from the below disclosure and from the examples provided herein, the variants themselves have interesting properties.

Thus, in its broadest aspect the present invention relates to novel variants of a parent protein C polypeptide, where the variants constitute the polypeptide part, more particularly the APC part, of the conjugates of the invention. As will be evident from the examples provided herein, it has been found that some variants, wherein one or more glycosylation sites were introduced, but not utilized, has interesting properties, in particular with respect to increased resistance towards inhibition by alpha-1-antitrypsin and increased resistance towards inactivation by human plasma. These variant comprises at least one substitution in the active site region (as defined in Example 2 herein), in particular they comprise a substitution of an amino acid residue, which is located in the active site region and which has at least 25% of its side chain exposed to the surface (as defined in Example 3 herein). Thus, preferred variants according to this aspect of the invention comprises a substitution in a position selected from the group consisting of D172, D189, S190, K191, K192, K193, D214, E215, S216, K217, K218, L220, V243, V245, S250, K251, S252, T253, T254, D255, L296, Y302, H303, S304, S305, S304, S305, R306, E307, K308, E309, A310, R312, T315, F316, V334, S336, N337, M338, I348, L349, D351, R352, E357, E382, G383, L386, L387 and H388, with the proviso that the substitution is not selected from the group consisting of T254S, T254A, T254H, T254K, T254R, T254N, T254D, T254E, T254G, T254Q, Y302S, Y302A, Y302T, Y302H, Y302K, Y302R, Y302N, Y302D, Y302E, Y302G, Y302Q, F316S, F316A, F316T, F316H, F316K, F316R, F316N, F316D, F316E, F316G and F316Q.

As is evident from the above list of positions, which are located in the active site region and, at the same time, has at least 25% of its side chain exposed to the surface, a significant amount of the these positions are occupied by charged amino acid residues. Analysing the three-dimensional structure of protein C, in particular the above-identified region, it can be observed that at least some of the charged residues interact with each other. For example, K251 is believed to form a salt bridge to D214. Moreover, it can be seen that a cluster of negatively charged amino acid residues (D214, E215 and E357) is present. Without being bound by any particular theory it is contemplated that the charged amino acid residues within the above-identified region, or at least some of the charged amino acid residues within this particular region, are important for capturing and/or binding the substrate/inhibitor. Therefore, amino acid substitutions which are particular interesting according to this aspect of the present invention are constituted by such an amino acid substitutions, wherein a charged amino acid residue, which is located in the active site region and, at the same time, has at least 25% of its side chain exposed to the surface, is substituted with an amino acid residue having no charge, in particular an amino acid residue having no charge but a polar side chain (Gly, Ser, Thr, Cys, Tyr, Asn or Gln), as well as amino acid substitutions, wherein a charged amino acid residue, which is located in the active site region and, at the same time, has at least 25% of its side chain exposed to the surface, is substituted with an amino acid residue having an opposite charge.

Specific examples of amino acid substitutions, wherein the charge of the amino acid residue in question is changed to an opposite charge, include D172K, D172R, D189K, D189R, K191D, K191E, K192D, K192E, K193D, K193E, D214K, D214R, E215K, E215R, K217D, K217E, K218D, K218E, K251 D, K251E, D255K, D255R, R306D, R306E, E307K, E307R, K308D, K308E, E309K, E309R, R312D, R312E, D351K, D351R, R352D, R352E, E357K, E357R, E382K and E382R, such as D214K, D214R, E215K, E215R, K251D, K251E, E357K and E357R, e.g. D214K, D214R, K251D and K251E, in particular K251D.

Other specific examples of amino acid substitutions, wherein the charged amino acid residue in question is substituted with an amino acid side chain having a polar side chain, include D172G/S/T/C/Y/N/Q, D189G/S/T/C/Y/N/Q, K191G/S/T/C/Y/N/Q, K192G/S/T/C/Y/N/Q, K193G/S/T/C/Y/N/Q, D214G/S/T/C/Y/N/Q, E215G/S/T/C/Y/N/Q, K217G/S/T/C/Y/N/Q, K218G/S/T/C/Y/N/Q, K251G/S/T/C/Y/N/Q, D255G/S/T/C/Y/N/Q, R306G/S/T/C/Y/N/Q, E307G/S/T/C/Y/N/Q, K308G/S/T/C/Y/N/Q, E309G/S/T/C/Y/N/Q, R312G/S/T/C/Y/N/Q, D351G/S/T/C/Y/N/Q, R352G/S/T/C/Y/N/Q, E357G/S/T/C/Y/N/Q and E382G/S/T/C/Y/N/Q, such as D214G/S/T/C/Y/N/Q, E215G/S/T/C/Y/N/Q, K251G/S/T/C/Y/N/Q and E357G/S/T/C/Y/N/Q, e.g. D214Q, E215Q, K251Q and E357Q, in particular K251Q. Another interesting substitution may be K251N+T253A.

Further specific examples of interesting substitutions include the substitutions disclosed in the sections entitled "Conjugate of the invention where the non-polypeptide moiety is a sugar moiety" and "Conjugate of the invention wherein the non-polypeptide moiety is attached to a cysteine residue", in particular the substitutions selected from the group consisting of K251N, S252N, Y302N and S190+ K192T, especially K251N and S252N, most preferably K251N.

As will be understood, details and particulars concerning the conjugates of the invention (e.g. activation of protein C, number of substitutions, formulation of conjugates, indications for which the conjugates may be used, increased resistance towards inactivation by alpha-1-antitrypsin and human plasma, etc.) will be the same or analogous to the variant aspect of the invention, whenever appropriate. Thus, statements and details concerning the conjugates of the invention will apply mutatis mutandis to the protein C variants disclosed herein, whenever appropriate.

Non-Polypeptide Moiety of the Conjugate of the Invention

As indicated further above the non-polypeptide moiety of the conjugate of the invention is preferably selected from the group consisting of a polymer molecule, a lipophilic compound, a sugar moiety (by way of in vivo glycosylation) and an organic derivatizing agent. All of these agents may confer desirable properties to the polypeptide part of the conjugate, in particular increased functional in vivo half-life and/or increased plasma half-life. The polypeptide part of the conjugate is normally conjugated to only one type of non-polypeptide moiety, but may also be conjugated to two or more different types of non-polypeptide moieties, e.g. to a polymer molecule and a sugar moiety, to a lipophilic group and a sugar moiety, to an organic derivatizing agent and a sugar moiety, to a lipophilic group and a polymer molecule, etc. The conjugation to two or more different non-polypeptide moieties may be done simultaneous or sequentially.

Methods of Preparing a Conjugate of the Invention

In the following sections "Conjugation to a lipophilic compound", "Conjugation to a polymer molecule", "Conjugation to a sugar moiety" and "Conjugation to an organic derivatizing agent" conjugation to specific types of non-polypeptide moieties is described. In general, a polypeptide conjugate according to the invention may be produced by culturing an appropriate host cell under conditions conducive for the expression of the polypeptide, and recovering the polypeptide, wherein a) the polypeptide comprises at least one N- or O-glycosylation site and the host cell is an eukaryotic host cell capable of in vivo glycosylation, and/or b) the polypeptide is subjected to conjugation to a non-polypeptide moiety in vitro.

It will be understood that the conjugation should be designed so as to produce the optimal molecule with respect to the number of non-polypeptide moieties attached, the size and form of such molecules (e.g. whether they are linear or branched), and the attachment site(s) in the polypeptide. The molecular weight of the non-polypeptide moiety to be used may e.g. be chosen on the basis of the desired effect to be achieved. For instance, if the primary purpose of the conjugation is to achieve a conjugate having a high molecular weight (e.g. to reduce renal clearance) it is usually desirable to conjugate as few high molecular weight non-polypeptide moieties as possible to obtain the desired molecular weight. When a high degree of shielding is desirable this may be obtained by use of a sufficiently high number of low molecular weight non-polypeptide moieties (e.g. with a molecular weight of from about 300 Da to about 5 kDa, such as a molecular weight of from 300 Da to 2 kDa).

Conjugation to a Polymer Molecule

The polymer molecule to be coupled to the polypeptide may be any suitable polymer molecule, such as a natural or synthetic homo-polymer or hetero-polymer, typically with a molecular weight in the range of about 300–100,000 Da, such as about 500–20,000 Da, more preferably in the range of about 500–15,000 Da, even more preferably in the range of about 2–12 kDa, such as in the range of about 3–10 kDa. When the term "about" is used herein in connection with a certain molecular weight, the word "about" indicates an approximate average molecular weight and reflects the fact that there will normally be a certain molecular weight distribution in a given polymer preparation.

Examples of homo-polymers include a polyol (i.e. poly-OH), a polyamine (i.e. poly-$NH_2$) and a polycarboxylic acid (i.e. poly-COOH). A hetero-polymer is a polymer comprising different coupling groups, such as a hydroxyl group and an amine group.

Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs, poly-vinyl alcohol (PVA), polycarboxylate, poly-(vinylpyrolidone), polyethylene-co-maleic acid anhydride, polystyrene-co-maleic acid anhydride, dextran, including carboxymethyl-dextran, or any other biopolymer suitable for reducing immunogenicity and/or increasing functional in vivo half-life and/or serum half-life. Another example of a polymer molecule is human albumin or another abundant plasma protein. Generally, polyalkylene glycol-derived polymers are biocompatible, non-toxic, non-antigenic, non-immunogenic, have various water solubility properties, and are easily excreted from living organisms.

PEG is the preferred polymer molecule, since it has only few reactive groups capable of cross-linking compared to, e.g., polysaccharides such as dextran. In particular, monofunctional PEG, e.g. methoxypolyethylene glycol (mPEG), is of interest since its coupling chemistry is relatively simple (only one reactive group is available for conjugating with attachment groups on the polypeptide). Consequently, the risk of cross-linking is eliminated, the resulting polypeptide conjugates are more homogeneous and the reaction of the polymer molecules with the polypeptide is easier to control.

To effect covalent attachment of the polymer molecule(s) to the polypeptide, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl succinamide (SSA), succinimidyl propionate (SPA), succinimidyl butyrate (SBA), succinimidy carboxymethylate (SCM), benzotriazole carbonate (BTC), N-hydroxysuccinimide (NHS), aldehyde, nitrophenyl-carbonate (NPC), and tresylate (TRES)). Suitable activated polymer molecules are commercially available, e.g. from Shearwater Polymers, Inc., Huntsville, Ala., USA, or from PolyMASC Phammaceuticals plc, UK.

Alternatively, the polymer molecules can be activated by conventional methods known in the art, e.g. as disclosed in WO 90/13540. Specific examples of activated linear or branched polymer molecules for use in the present invention are described in the Shearwater Polymers, Inc. 1997 and 2000 Catalogs (Functionalized Biocompatible Polymers for Research and pharmaceuticals, Polyethylene Glycol and Derivatives, incorporated herein by reference).

Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG, BTC-PEG, EPOX-PEG, NCO-PEG, NPC-PEG, CDI-PEG, ALD-PEG, TRES-PEG, VS-PEG, IODO-PEG and MAL-PEG, including the mPEG forms thereof, and branched PEGs such as PEG2-NHS, including the mPEG forms thereof, and those disclosed in U.S. Pat. No. 5,932,462 and U.S. Pat. No. 5,643,575, both of which are incorporated herein by reference. Furthermore, the following publications, incorporated herein by reference, disclose useful polymer molecules and/or PEGylation chemistries: U.S. Pat. No. 5,824,778, U.S. Pat. No. 5,476,653, WO 97/32607, EP 229,108, EP 402,378, U.S. Pat. No. 4,902,502, U.S. Pat. No. 5,281,698, U.S. Pat. No. 5,122,614, U.S. Pat. No. 5,219,564, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. No. 5,473,034, U.S. Pat. No. 5,516,673, EP 605 963, U.S. Pat. No. 5,382,657, EP 510 356, EP 400 472, EP 183 503 and EP 154 316.

The conjugation of the polypeptide and the activated polymer molecules is conducted by use of any conventional method, e.g. as described in the following references (which also describe suitable methods for activation of polymer molecules): R. F. Taylor, (1991), "Protein immobilisation. Fundamental and applications", Marcel Dekker, N. Y.; S. S. Wong, (1992), "Chemistry of Protein Conjugation and Crosslinking", CRC Press, Florida, USA; G. T. Hermanson et al., (1993), "Immobilized Affinity Ligand Techniques", Academic Press, N.Y.). The skilled person will be aware that the activation method and/or conjugation chemistry to be used depends on the attachment group(s) of the polypeptide (examples of which are given further above), as well as the functional groups of the polymer (e.g. being amine, hydroxyl, carboxyl, aldehyde, sulfydryl, succinimidyl, maleimide, vinysulfone or haloacetate). The PEGylation may be directed towards conjugation to all available attachment groups on the polypeptide (i.e. such attachment groups that are exposed at the surface of the polypeptide) or may be directed towards one or more specific attachment groups, e.g. the N-terminal amino group as described in U.S. Pat. No. 5,985,265. Furthermore, the conjugation may be achieved in one step or in a stepwise manner (e.g. as described in WO 99/55377).

It will be understood that the PEGylation is designed so as to produce the optimal molecule with respect to the number of PEG molecules attached, the size and form of such molecules (e.g. whether they are linear or branched), and the attachment site(s) in the polypeptide. The molecular weight of the polymer to be used may e.g. be chosen on the basis of the desired effect to be achieved.

In connection with conjugation to only a single attachment group on the protein (e.g. the N-terminal amino group), it may be advantageous that the polymer molecule, which may be linear or branched, has a high molecular weight, preferably about 10–25 kDa, such as about 15–25 kDa, e.g. about 20 kDa.

Normally, the polymer conjugation is performed under conditions aimed at reacting as many of the available polymer attachment groups with polymer molecules. This is achieved by means of a suitable molar excess of the polymer relative to the polypeptide. Typically, the molar ratios of activated polymer molecules to polypeptide are up to about 1000–1, such as up to about 200–1, or up to about 100–1. In some cases the ration may be somewhat lower, however, such as up to about 50–1, 10–1, 5–1, 2–1 or 1–1 in order to obtain optimal reaction.

It is also contemplated according to the invention to couple the polymer molecules to the polypeptide through a linker. Suitable linkers are well known to the skilled person. A preferred example is cyanuric chloride (Abuchowski et al., (1977), J. Biol. Chem., 252, 3578–3581; U.S. Pat. No. 4,179,337; Shafer et al., (1986), J. Polym. Sci. Polym. Chem. Ed., 24, 375–378).

Subsequent to the conjugation, residual activated polymer molecules are blocked according to methods known in the art, e.g. by addition of primary amine to the reaction mixture, and the resulting inactivated polymer molecules are removed by a suitable method.

It will be understood that depending on the circumstances, e.g. the amino acid sequence of the polypeptide, the nature of the activated PEG compound being used and the specific PEGylation conditions, including the molar ratio of PEG to polypeptide, varying degrees of PEGylation may be obtained, with a higher degree of PEGylation generally being obtained with a higher ratio of PEG to polypeptide. The PEGylated polypeptides resulting from any given PEGylation process will, however, normally comprise a stochastic distribution of polypeptide conjugates having slightly different degrees of PEGylation.

Coupling to a Sugar Moiety

In order to achieve in vivo glycosylation of a protein C molecule comprising one or more glycosylation sites the nucleotide sequence encoding the polypeptide must be inserted in a glycosylating, eucaryotic expression host. The expression host cell may be selected from fungal (filamentous fungal or yeast), insect or animal cells or from transgenic plant cells. In one embodiment the host cell is a mammalian cell, such as a COS cell, a CHO cell, a BHK cell or a HEK cell, e.g. a HEK 293 cell, or an insect cell, such as an SF9 cell, or a yeast cell, e.g. *S. cerevisiae* or *Pichia pastoris*, or any of the host cells mentioned hereinafter.

Covalent in vitro coupling of sugar moieties (such as dextran) to amino acid residues of the polypeptide may also be used, e.g. as described, for example in WO 87/05330 and in Aplin et al., CRC Crit Rev. Biochem, pp. 259–306, 1981. The in vitro coupling of sugar moieties or PEG to protein- and peptide-bound Gln-residues can be carried out by transglutaminases (TGases). Transglutaminases catalyse the transfer of donor amine-groups to protein- and peptide-bound Gln-residues in a so-called cross-linking reaction. The donor-amine groups can be protein- or peptide-bound, such as the $\epsilon$-amino-group in Lys-residues or it can be part of a small or large organic molecule. An example of a small organic molecule functioning as amino-donor in TGase-catalysed cross-linking is putrescine (1,4-diaminobutane). An example of a larger organic molecule functioning as amino-donor in TGase-catalysed cross-linking is an amine-containing PEG (Sato et al., 1996, Biochemistry 35, 13072–13080).

TGases, in general, are highly specific enzymes, and not every Gln-residues exposed on the surface of a protein is accessible to TGase-catalysed cross-linking to amino-containing substances. On the contrary, only few Gln-residues are naturally functioning as TGase substrates but the exact parameters governing which Gln-residues are good TGase substrates remain unknown. Thus, in order to render a protein susceptible to TGase-catalysed cross-linking reactions it is often a prerequisite at convenient positions to add stretches of amino acid sequence known to function very well as TGase substrates. Several amino acid sequences are known to be or to contain excellent natural TGase substrates e.g. substance P, elafin, fibrinogen, fibronectin, $\alpha_2$-plasmin inhibitor, $\alpha$-caseins, and $\beta$-caseins.

Conjugation to an Organic Derivatizing Agent

Covalent modification of the polypeptide may be performed by reacting one or more attachment groups of the polypeptide with an organic derivatizing agent. Suitable derivatizing agents and methods are well known in the art. For example, cysteinyl residues most commonly are reacted with $\alpha$-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, $\alpha$-bromo-$\beta$-(4-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues are derivatized by reaction with diethylpyrocarbonate at pH 5.5–7.0 because this agent is relatively specific for the histidyl side chain. Parabromophenacyl bromide also is useful. The reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues. Other suitable reagents for derivatizing $\alpha$-amino-containing residues include imidoesters such as methyl picolinimidate, pyridoxal phosphate, pyridoxal, chloroborohydride, trinitrobenzenesulfonic acid, O-methylisourea, 2,4-pentanedione and transaminase-catalyzed reaction with glyoxylate. Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine guanidino group. Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Conjugation to a Lipophilic Compound

The polypeptide and the lipophilic compound may be conjugated to each other, either directly or by use of a linker. The lipophilic compound may be a natural compound such as a saturated or unsaturated fatty acid, a fatty acid diketone, a terpene, a prostaglandin, a vitamine, a carotenoide or steroide, or a synthetic compound such as a carbon acid, an alcohol, an amine and sulphonic acid with one or more alkyl-, aryl-, alkenyl- or other multiple unsaturated compounds. The conjugation between the polypeptide and the lipophilic compound, optionally through a linker may be done according to methods known in the art, e.g. as described by Bodanszky in Peptide Synthesis, John Wiley, New York, 1976 and in WO 96/12505.

Conjugation of a Tagged Polypeptide

The polypeptide may be expressed as a fusion protein with a tag, i.e. an amino acid sequence or peptide stretch made up of typically 1–30, such as 1–20 amino acid residues. Besides allowing for fast and easy purification, the tag is a convenient tool for achieving conjugation between the tagged polypeptide and the non-polypeptide moiety. In particular, the tag may be used for achieving conjugation in microtiter plates or other carriers, such as paramagnetic beads, to which the tagged polypeptide can be immobilised via the tag. The conjugation to the tagged polypeptide in, e.g., microtiter plates has the advantage that the tagged polypeptide can be immobilised in the microtiter plates directly from the culture broth (in principle without any purification) and subjected to conjugation. Thereby, the total number of process steps (from expression to conjugation) can be reduced. Furthermore, the tag may function as a spacer molecule, ensuring an improved accessibility to the immobilised polypeptide to be conjugated. The conjugation using a tagged polypeptide may be to any of the non-polypeptide moieties disclosed herein, e.g. to a polymer molecule such as PEG.

The identity of the specific tag to be used is not critical as long as the tag is capable of being expressed with the polypeptide and is capable of being immobilised on a suitable surface or carrier material. A number of suitable tags are commercially available, e.g. from Unizyme Laboratories, Denmark. For instance, the tag may consist of any of the following sequences:

```
His-His-His-His-His-His              (SEQ ID NO:41);

Met-Lys-His-His-His-His-His          (SEQ ID NO:42);

Met-Lys-His-His-Ala-His-His-Gln-     (SEQ ID NO:43);
His-His

Met-Lys-His-Gln-His-Gln-His-Gln-     (SEQ ID NO:44);
His-Gln-His-Gln-His-Gln

Met-Lys-His-Gln-His-Gln-His-Gln-     (SEQ ID NO:45);
His-Gln-His-Gln-His-Gln-Gln
``` or any of the following:

```
EQKLI SEEDL (SEQ ID NO:46; a C-terminal tag
            described in Mol. Cell. Biol. 5: 3610-
            16, 1985);

DYKDDDDK    (SEQ ID NO:47; a C- or N-terminal tag);
            and

YPYDVPDYA   (SEQ ID NO:48).
```

Antibodies against the above tags are commercially available, e.g. from ADI, Aves Lab and Research Diagnostics.

The subsequent cleavage of the tag from the polypeptide may be achieved by use of commercially available enzymes.

Methods of Preparing a Polypeptide Variant of the Invention or the Polypeptide Part of the Conjugate of the Invention The polypeptide variant of the present invention or the polypeptide part of a conjugate of the invention, optionally in glycosylated form, may be produced by any suitable method known in the art. Such methods include constructing a nucleotide sequence encoding the polypeptide and expressing the sequence in a suitable transformed or transfected host. Preferably, the host cell is a gammacarboxylating host cell such as a mammalian cell. However, polypeptides of the invention may be produced, albeit less efficiently, by chemical synthesis or a combination of chemical synthesis or a combination of chemical synthesis and recombinant DNA technology.

A nucleotide sequence encoding a polypeptide variant or the polypeptide part of a conjugate of the invention may be constructed by isolating or synthesizing a nucleotide sequence encoding the parent protein C, such as protein C with the amino acid sequence shown in SEQ ID NO:2 and 4 and then changing the nucleotide sequence so as to effect introduction (i.e. insertion or substitution) or removal (i.e. deletion or substitution) of the relevant amino acid residue(s).

The nucleotide sequence is conveniently modified by site-directed mutagenesis in accordance with conventional methods. Alternatively, the nucleotide sequence is prepared by chemical synthesis, e.g. by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction (LCR) (Barany, PNAS 88:189–193, 1991). The individual oligonucleotides typically contain 5' or 3' overhangs for complementary assembly.

Alternative nucleotide sequence modification methods are available for producing polypeptide variants for high throughput screening, for instance methods which involve homologous cross-over such as disclosed in U.S. Pat. No. 5,093,257, and methods which involve gene shuffling, i.e. recombination between two or more homologous nucleotide sequences resulting in new nucleotide sequences having a number of nucleotide alterations when compared to the starting nucleotide sequences. Gene shuffling (also known as DNA shuffling) involves one or more cycles of random fragmentation and reassembly of the nucleotide sequences, followed by screening to select nucleotide sequences encoding polypeptides with desired properties. In order for homology-based nucleic acid shuffling to take place, the relevant parts of the nucleotide sequences are preferably at least 50% identical, such as at least 60% identical, more preferably at least 70% identical, such as at least 80% identical. The recombination can be performed in vitro or in vivo.

Examples of suitable in vitro gene shuffling methods are disclosed by Stemmer et al. (1994), Proc. Natl. Acad. Sci. USA; vol. 91, pp. 10747–10751; Stemmer (1994), Nature, vol. 370, pp. 389–391; Smith (1994), Nature vol. 370, pp. 324–325; Zhao et al., Nat. Biotechnol. 1998, March; 16(3): 258–61; Zhao H. and Arnold, F B, Nucleic Acids Research, 1997, Vol. 25. No. 6 pp. 1307–1308; Shao et al., Nucleic Acids Research 1998, Jan. 15; 26(2): pp. 681–83; and WO 95/17413.

An example of a suitable in vivo shuffling method is disclosed in WO 97/07205. Other techniques for mutagenesis of nucleic acid sequences by in vitro or in vivo recombination are disclosed e.g. in WO 97/20078 and U.S. Pat. No. 5,837,458. Examples of specific shuffling techniques include "family shuffling", "synthetic shuffling" and "in silico shuffling".

Family shuffling involves subjecting a family of homologous genes from different species to one or more cycles of shuffling and subsequent screening or selection. Family shuffling techniques are disclosed e.g. by Crameri et al. (1998), Nature, vol. 391, pp. 288–291; Christians et al. (1999), Nature Biotechnology, vol. 17, pp. 259–264; Chang et al. (1999), Nature Biotechnology, vol. 17, pp. 793–797; and Ness et al. (1999), Nature Biotechnology, vol. 17, 893–896.

Synthetic shuffling involves providing libraries of overlapping synthetic oligonucleotides based e.g. on a sequence alignment of homologous genes of interest. The synthetically generated oligonucleotides are recombined, and the resulting recombinant nucleic acid sequences are screened and if desired used for further shuffling cycles. Synthetic shuffling techniques are disclosed in WO 00/42561.

In silico shuffling refers to a DNA shuffling procedure, which is performed or modelled using a computer system, thereby partly or entirely avoiding the need for physically manipulating nucleic acids. Techniques for in silico shuffling are disclosed in WO 00/42560. Once assembled (by synthesis, site-directed mutagenesis or another method), the nucleotide sequence encoding the polypeptide is inserted into a recombinant vector and operably linked to control sequences necessary for expression of protein C in the desired transformed host cell.

It should of course be understood that not all vectors and expression control sequences function equally well to express the nucleotide sequence encoding a polypeptide described herein. Neither will all hosts function equally well with the same expression system. However, one of skill in the art may make a selection among these vectors, expression control sequences and hosts without undue experimentation. For example, in selecting a vector, the host must be considered because the vector must replicate in it or be able to integrate into the chromosome. The vector's copy number, the ability to control that copy number, and the expression of any other proteins encoded by the vector, such as antibiotic markers, should also be considered. In selecting an expression control sequence, a variety of factors should also be considered. These include, for example, the relative strength of the sequence, its controllability, and its compatibility with the nucleotide sequence encoding the polypeptide, particularly as regards potential secondary structures. Hosts should be selected by consideration of their compatibility with the chosen vector, the toxicity of the product coded for by the nucleotide sequence, their secretion characteristics, their ability to fold the polypeptide correctly, their fermentation or culture requirements, and the ease of purification of the products coded for by the nucleotide sequence.

The recombinant vector may be an autonomously replicating vector, i.e. a vector, which exists as an extrachromosomal entity, the replication of which is independent of chromosomal replication, e.g. a plasmid. Alternatively, the vector is one which, when introduced into a host cell, is integrated into the host cell genome and replicated together with the chromosome(s) into which it has been integrated.

The vector is preferably an expression vector, in which the nucleotide sequence encoding the polypeptide of the invention is operably linked to additional segments required for transcription of the nucleotide sequence. The vector is typically derived from plasmid or viral DNA. A number of suitable expression vectors for expression in the host cells mentioned herein are commercially available or described in the literature. Useful expression vectors for eukaryotic hosts, include, for example, vectors comprising expression control sequences from SV40, bovine papilloma virus, adenovirus and cytomegalovirus. Specific vectors are, e.g., pCDNA3.1 (+)\Hyg (Invitrogen, Carlsbad, Calif., USA) and pCl-neo (Stratagene, La Jola, Calif., USA). Useful expression vectors for yeast cells include the 2μ plasmid and derivatives thereof, the POT1 vector (U.S. Pat. No. 4,931,373), the pJSO37 vector described in Okkels, Ann. New York Acad. Sci. 782, 202–207, 1996, and pPICZ A, B or C (Invitrogen). Useful vectors for insect cells include pVL941, pBG311 (Cate et al., "Isolation of the Bovine and Human Genes for Mullerian Inhibiting Substance And Expression of the Human Gene In Animal Cells", Cell, 45, pp. 685–98 (1986), pBluebac 4.5 and pMelbac (both available from Invitrogen). Useful expression vectors for bacterial hosts include known bacterial plasmids, such as plasmids from *E. coli*, including pBR322, pET3a and pET12a (both from Novagen Inc., Wis., USA), wider host range plasmids, such as RP4, phage DNAs, e.g., the numerous derivatives of phage lambda, e.g., NM989, and other DNA phages, such as M13 and filamentous single stranded DNA phages.

Other vectors for use in this invention include those that allow the nucleotide sequence encoding the polypeptide to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrafolate Reductase cDNA Gene: Analysis Of Signals Utilized For Efficient Expression", Mol. Cell. Biol., 2, pp. 1304–19 (1982)) and glutamine synthetase ("GS") amplification (see, e.g., U.S. Pat. No. 5,122,464 and EP 338,841).

The recombinant vector may further comprise a DNA sequence enabling the vector to replicate in the host cell in question. An example of such a sequence (when the host cell is a mammalian cell) is the SV40 origin of replication. When the host cell is a yeast cell, suitable sequences enabling the vector to replicate are the yeast plasmid 2μ replication genes REP 1–3 and origin of replication.

The vector may also comprise a selectable marker, e.g. a gene the product of which complements a defect in the host cell, such as the gene coding for dihydrofolate reductase (DHFR) or the Schizosaccharomyces pombe TPI gene (described by P. R. Russell, Gene 40, 1985, pp. 125–130), or one which confers resistance to a drug, e.g. ampicillin, kanamycin, tetracyclin, chloramphenicol, neomycin, hygromycin or methotrexate. For *Saccharomyces cerevisiae*, selectable markers include ura3 and leu2. For filamentous fungi, selectable markers include amdS, pyrG, arcB, niaD and sC.

The term "control sequences" is defined herein to include all components, which are necessary or advantageous for the expression of the polypeptide of the invention. Each control sequence may be native or foreign to the nucleic acid sequence encoding the polypeptide. Such control sequences include, but are not limited to, a leader sequence, polyadenylation sequence, propeptide sequence, promoter, enhancer or upstream activating sequence, signal peptide sequence, and transcription terminator. At a minimum, the control sequences include a promoter.

A wide variety of expression control sequences may be used in the present invention. Such useful expression control sequences include the expression control sequences associated with structural genes of the foregoing expression vectors as well as any sequence known to control the expression of genes of prokaryotic or eukaryotic cells or their viruses, and various combinations thereof.

Examples of suitable control sequences for directing transcription in mammalian cells include the early and late promoters of SV40 and adenovirus, e.g. the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus E1b region polyadenylation signals and the Kozak consensus sequence (Kozak, M. J Mol Biol 1987 Aug. 20;196(4):947–50).

In order to improve expression in mammalian cells a synthetic intron may be inserted in the 5' untranslated region of the nucleotide sequence encoding the polypeptide. An example of a synthetic intron is the synthetic intron from the plasmid pCI-Neo (available from Promega Corporation, Wis., USA).

Examples of suitable control sequences for directing transcription in insect cells include the polyhedrin promoter, the P10 promoter, the *Autographa californica* polyhedrosis virus basic protein promoter, the baculovirus immediate early gene 1 promoter and the baculovirus 39K delayed-early gene promoter, and the SV40 polyadenylation sequence. Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4c promoter, and the inducible GAL promoter. Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger*

α-amylase, *A. niger* or *A. nidulans* glucoamylase, *A. nidulans* acetamidase, *Rhizomucor miehei* aspartic proteinase or lipase, the TPI1 terminator and the ADH3 terminator. Examples of suitable control sequences for use in bacterial host cells include promoters of the lac system, the trp system, the TAC or TRC system, and the major promoter regions of phage lambda.

The presence or absence of a signal peptide will, e.g., depend on the expression host cell used for the production of the polypeptide to be expressed (whether it is an intracellular or extracellular polypeptide) and whether it is desirable to obtain secretion. For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase. For use in insect cells, the signal peptide may conveniently be derived from an insect gene (cf. WO 90/05783), such as the Lepidopteran manduca sexta adipokinetic hormone precursor, (cf. U.S. Pat. No. 5,023,328), the honeybee melittin (Invitrogen), ecdysteroid UDPglucosyltransferase (egt) (Murphy et al., Protein Expression and Purification 4, 349–357 (1993) or human pancreatic lipase (hpl) (Methods in Enzymology 284, pp. 262–272,1997). A preferred signal peptide for use in mammalian cells is that of hFVII or the murine Ig kappa light chain signal peptide (Coloma, M (1992) J. Imm. Methods 152:89–104). For use in yeast cells suitable signal peptides have been found to be the α-factor signal peptide from *S. cereviciae* (cf. U.S. Pat. No. 4,870,008), a modified carboxypeptidase signal peptide (cf. L. A. Valls et al., Cell 48, 1987, pp. 887–897), the yeast BAR1 signal peptide (cf. WO 87/02670), the yeast aspartic protease 3 (YAP3) signal peptide (cf. M. Egel-Mitani et al., Yeast 6, 1990, pp. 127–137), and the synthetic leader sequence TA57 (WO98/32867). For use in *E. coli* cells a suitable signal peptide have been found to be the signal peptide ompA (EP581821).

The nucleotide sequence of the invention encoding a protein C polypeptide variant, whether prepared by site-directed mutagenesis, synthesis, PCR or other methods, may optionally include a nucleotide sequence that encode a signal peptide. The signal peptide is present when the polypeptide is to be secreted from the cells in which it is expressed. Such signal peptide, if present, should be one recognized by the cell chosen for expression of the polypeptide. The signal peptide may be homologous (e.g. be that normally associated with human protein C) or heterologous (i.e. originating from another source than human protein C) to the polypeptide or may be homologous or heterologous to the host cell, i.e. be a signal peptide normally expressed from the host cell or one which is not normally expressed from the host cell. Accordingly, the signal peptide may be prokaryotic, e.g. derived from a bacterium such as *E. coli*, or eukaryotic, e.g. derived from a mammalian, or insect or yeast cell.

Any suitable host may be used to produce the polypeptide or polypeptide part of the conjugate of the invention, including bacteria, fungi (including yeasts), plant, insect, mammal, or other appropriate animal cells or cell lines, as well as transgenic animals or plants. Examples of bacterial host cells include grampositive bacteria such as strains of *Bacillus*, e.g. *B. brevis* or *B. subtilis*, *Pseudomonas* or *Streptomyces*, or gramnegative bacteria, such as strains of *E. coli*. The introduction of a vector into a bacterial host cell may, for instance, be effected by protoplast transformation (see, e.g., Chang and Cohen, 1979, Molecular General Genetics 168: 111–115), using competent cells (see, e.g., Young and Spizizin, 1961, Journal of Bacteriology 81: 823–829, or Dubnau and Davidoff-Abelson, 1971, Journal of Molecular Biology 56: 209–221), electroporation (see, e.g., Shigekawa and Dower, 1988, Biotechniques 6: 742–751), or conjugation (see, e.g., Koehler and Thorne, 1987, Journal of Bacteriology 169: 5771–5278). Examples of suitable filamentous fungal host cells include strains of *Aspergillus*, e.g. *A. oryzae*, *A. niger*, or *A. nidulans*, *Fusarium* or *Trichoderma*. Fungal cells may be transformed by a process involving protoplast formation, transformation of the protoplasts, and regeneration of the cell wall in a manner known per se. Suitable procedures for transformation of *Aspergillus* host cells are described in EP 238 023 and U.S. Pat. No. 5,679,543. Suitable methods for transforming *Fusarium* species are described by Malardier et al., 1989, Gene 78: 147–156 and WO 96/00787. Examples of suitable yeast host cells include strains of *Saccharomyces*, e.g. *S. cerevisiae*, *Schizosaccharomyces*, *Klyveromyces*, *Pichia*, such as *P. pastoris* or *P. methanolica*, *Hansenula*, such as *H. Polymorpha* or *Yarrowia*. Yeast may be transformed using the procedures described by Becker and Guarente, In Abelson, J. N. and Simon, M. I., editors, Guide to Yeast Genetics and Molecular Biology, Methods in Enzymology, Volume 194, pp 182–187, Academic Press, Inc., New York; Ito et al., 1983, Journal of Bacteriology 153: 163; Hinnen et al., 1978, Proceedings of the National Academy of Sciences USA 75: 1920: and as disclosed by Clontech Laboratories, Inc, Palo Alto, Calif., USA (in the product protocol for the Yeastmaker™ Yeast Transformation System Kit). Examples of suitable insect host cells include a *Lepidoptora* cell line, such as *Spodoptera frugiperda* (Sf9 or Sf21) or *Trichoplusioa ni* cells (High Five) (U.S. Pat. No. 5,077,214). Transformation of insect cells and production of heterologous polypeptides therein may be performed as described by Invitrogen. Examples of suitable mammalian host cells include Chinese hamster ovary (CHO) cell lines, (e.g. CHO-K1; ATCC CCL-61), Green Monkey cell lines (COS) (e.g. COS 1 (ATCC CRL-1650), COS 7 (ATCC CRL-1651)); mouse cells (e.g. NS/0), Baby Hamster Kidney (BHK) cell lines (e.g. ATCC CRL-1632 or ATCC CCL-10), and human cells (e.g. HEK 293 (ATCC CRL-1573)), as well as plant cells in tissue culture. Additional suitable cell lines are known in the art and available from public depositories such as the American Type Culture Collection, Rockville, Md. Also, the mammalian cell, such as a CHO cell, may be modified to express sialyltransferase, e.g. 1,6-sialyltransferase, e.g. as described in U.S. Pat. No. 5,047,335, in order to provide improved glycosylation of the protein C polypeptide.

In order to increase secretion it may be of particular interest to produce the polypeptide of the invention together with an endoprotease, in particular a PACE (Paired basic amino acid converting enzyme) (e.g. as described in U.S. Pat. No. 5,986,079), such as a Kex2 endoprotease (e.g. as described in WO 00/28065).

Methods for introducing exogeneous DNA into mammalian host cells include calcium phosphate-mediated transfection, electroporation, DEAE-dextran mediated transfection, liposome-mediated transfection, viral vectors and the transfection method described by Life Technologies Ltd, Paisley, UK using Lipofectamin 2000. These methods are well known in the art and e.g. described by Ausbel et al. (eds.), 1996, Current Protocols in Molecular Biology, John Wiley & Sons, New York, USA. The cultivation of mammalian cells are conducted according to established methods, e.g. as disclosed in (Animal Cell Biotechnology, Methods and Protocols, Edited by Nigel Jenkins, 1999, Human Press Inc, Totowa, N.J., USA and Harrison M A and Rae I F, General Techniques of Cell Culture, Cambridge University Press 1997).

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide may be recovered by methods known in the art. For example, the polypeptide may be recovered from the nutrient medium by conventional procedures including, but not limited to, centrifugation, filtration, ultra-filtration, extraction or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation) or extraction (see, e.g., Protein Purification, J.-C. Janson and Lars Ryden, editors, VCH Publishers, New York, 1989).

Pharmaceutical Compositions and Use

In a further aspect, the present invention relates to a pharmaceutical composition comprising a conjugate of the invention or a variant of the invention and a pharmaceutically acceptable carrier or excipient. In the present context, the term "Pharmaceutically acceptable" means that the carrier or excipient, at the dosages and concentrations employed, will not cause any unwanted or harmful effects in the patients to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]).

In a still further aspect, the present invention relates to a conjugate of the invention, a variant of the invention or a pharmaceutical composition of the invention for use as a medicament. More particularly, the conjugates, variants or pharmaceutical compositions of the invention may be used for the manufacture of a medicament for the treatment of stroke; myocardial infarction; after venous thrombosis; disseminated intravascular coagulation (DIC); sepsis; septic shock; emboli, such as pulmonary emboli; transplantation, such as bone marrow transplantation; burns; pregnancy; major surgery/traum or adult respiratory stress syndrome (ARDS), in particular for the treatment of septic shock.

The present invention also relates to a method for treating or preventing a disease selected from the group consisting of stroke; myocardial infarction; after venous thrombosis; disseminated intravascular coagulation (DIC); sepsis; septic shock; emboli, such as pulmonary emboli; transplantation, such as bone marrow transplantation; burns; pregnancy; major surgery/traum and adult respiratory stress syndrome (ARDS), the method comprising administering to a patient in need thereof an effective amount of a conjugate of the invention, of a variant according to the invention, or of a pharmaceutical composition according to the invention, in particular for treating or preventing, especially treating, septic shock.

A "patient" for the purposes of the present invention includes both humans and other mammals. Thus the methods are applicable to both human therapy and veterinary applications.

The polypeptide variants and conjugates of the invention will be administered to patients in an effective dose. By "effective dose" herein is meant a dose that is sufficient to produce the desired effects in relation to the condition for which it is administered. The exact dose will depend on the disorder to be treated, and will be ascertainable by one skilled in the art using known techniques. As mentioned above, in the treatment of severe sepsis 24 μg/kg/h of human APC is administered for 96 hours, which corresponds to a total amount of protein of about 230 mg for a patient having a body weight of about 100 kg. The conjugates and variants of the present invention are, due to their increased plasma half-lives, contemplated to have a higher efficacy due to the extended action-time in plasma. This increased efficacy may, for example, be estimated by calculating the area under the curve (AUC) in the "Human Plasma Inactivation assay II" or by measuring the serum half-life. The increased efficacy means that the effective dose needed to obtain the desired effect for a particular disorder will be smaller (less protein need to be administered) than the effective dose of human APC. In addition, the increased plasma half-life will also allow treatment where the APC variants or conjugates are used regularly with a given time-period. Thus, these new properties will permit the use of a reduced amount and/or and less frequent administration, such as bolus injections, of the compounds of the invention. For example, the compounds of the invention may be administered by a either a bolus or infusion or as a combination thereof with doses which range from 1 μg/kg body weight as a bolus every $2^{nd}$ hour for several days (e.g. for 96 hours) to 1 mg/kg body weight as a bolus once every $4^{th}$ day. Preferably, as low a dose as possible is administered as less frequent as possible, e.g. 1–500 μg/kg body weight, preferably 1–250 μg/kg body weight, such as 1–100 μg/kg body weight, more preferably 1–50 μg/kg body weight is administered as a bolus every 4–96 hour, e.g. every 8–96 hour, such as every 16–96, every 24–96 hour, every 40–96 hour, every 48–96 hour, every 56–96 hour, every 72–96 hour.

Compounds of the invention, which are preferred are such compounds where the ratio between the AUC of said compound, in its activated form, and the AUC of human APC is at least 1.25 when tested in the "Human Plasma Inactivation Assay II" described in Example 13 herein. Preferably, the ratio is at least 1.5, such as at least 2, e.g. at least 3, more preferably the ratio is at least 4, such as at least 5, e.g. at least 6, even more preferably the ratio is at least 7, such as at least 8, e.g. at least 9, most preferably the ratio is at least 10.

The polypeptide variant or conjugate of the invention can be used "as is" and/or in a salt form thereof. Suitable salts include, but are not limited to, salts with alkali metals or alkaline earth metals, such as sodium, potassium, calcium and magnesium, as well as e.g. zinc salts. These salts or complexes may by present as a crystalline and/or amorphous structure.

The pharmaceutical composition of the invention may be administered alone or in conjunction with other therapeutic agents. These agents may be incorporated as part of the same pharmaceutical composition or may be administered separately from the polypeptide or conjugate of the invention, either concurrently or in accordance with another treatment schedule. In addition, the polypeptide, conjugate or pharmaceutical composition of the invention may be used as an adjuvant to other therapies.

The pharmaceutical composition of the invention may be formulated in a variety of forms, e.g. as a liquid, gel, lyophilized, or as a compressed solid. The preferred form will depend upon the particular indication being treated and will be readily able to be determined by one skilled in the art.

The administration of the formulations of the present invention can be performed in a variety of ways, including, but not limited to, orally, subcutaneously, intravenously, intracerebrally, intranasally, transdermally, intraperitoneally, intramuscularly, intrapulmonary, vaginally, rectally, intraocularly, or in any other acceptable manner. The formulations can be administered continuously by infusion, although bolus injection is acceptable, using techniques well known in the art, such as pumps or implantation. In some instances the formulations may be directly applied as a solution or spray.

Parenteral Compositions

An example of a pharmaceutical composition is a solution designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

In case of parenterals, they are prepared for storage as lyophilized formulations or aqueous solutions by mixing, as appropriate, the polypeptide having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from about 2 mM to about 50 mM Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris. Preservatives are added to retard microbial growth, and are typically added in amounts of e.g. about 0.1%–2% (w/v). Suitable preservatives for use with the present invention include phenol, benzyl alcohol, meta-cresol, methyl paraben, propyl paraben, octadecyldimethylbenzyl ammonium chloride, benzalkonium halides (e.g. benzalkonium chloride, bromide or iodide), hexamethonium chloride, alkyl parabens such as methyl or propyl paraben, catechol, resorcinol, cyclohexanol and 3-pentanol.

Isotonicifiers are added to ensure isotonicity of liquid compositions and include polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, omithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, α-monothioglycerol and sodium thiosulfate; low molecular weight polypeptides (i.e. <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active protein weight.

Non-ionic surfactants or detergents (also known as "wetting agents") may be present to help solubilize the therapeutic agent as well as to protect the therapeutic polypeptide against agitation-induced aggregation, which also permits the formulation to be exposed to shear surface stress without causing denaturation of the polypeptide. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.).

Additional miscellaneous excipients include bulking agents or fillers (e.g. starch), chelating agents (e.g. EDTA), antioxidants (e.g., ascorbic acid, methionine, vitamin E) and cosolvents.

The active ingredient may also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions. Such techniques are disclosed in Remington's Pharmaceutical Sciences, supra.

Parenteral formulations to be used for in vivo administration must be sterile. This is readily accomplished, for example, by filtration through sterile filtration membranes.

Sustained Release Preparations

Suitable examples of sustained-release preparations include semi-permeable matrices of solid hydrophobic polymers containing the polypeptide or conjugate, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the ProLease® technology or Lupron Depot® (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for long periods such as up to or over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Figure 1:
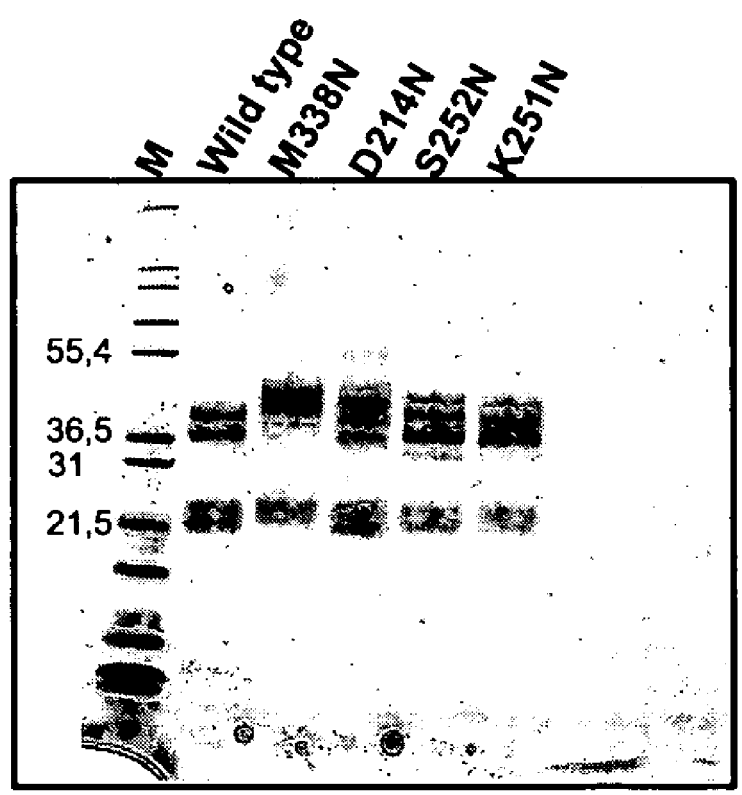
FIG. 1 shows purified wild-type human APC as well as various conjugates and variants of the invention. The proteins migrates on the gel as three dominate bands corresponding to the α- and β-bands of the heavy chain, with an apparent molecular weight of 41,000 and 37,000 respectively, and the light chain with an apparent molecular weight of 22,000. The degree of glycosylation can also be analysed from the gel shown in FIG. 1 as the migration of the heavy chains of the conjugates D214N and M338N shifted to more cathodal positions (contrary to the variants K251N and S252N which apparently did not utilize their introduced glycosylation site) showing that these two variants are glycosylated and the site is fully utilized. From the examination of the mobility of the heavy chain subforms (α and β), it is evident that the molecular weight of the carbohydrate side chains at each site is about 3,000 to 4,000.

The invention is further illustrated by the following, non-limiting, examples.

Methods

Accessible Surface Area (ASA)

The computer program Access (B. Lee and F. M. Richards, J. Mol. Biol. 55: 379–400 (1971)) version 2 (© 1983 Yale University) is used to compute the accessible surface area (ASA) of the individual atoms in the structure. This method typically uses a probe-size of 1.4Å and defines the Accessible Surface Area (ASA) as the area formed by the center of the probe. Prior to this calculation all water molecules and all hydrogen atoms are be removed from the coordinate set. Other atoms not directly related to the protein are also removed.

Fractional ASA of Side Chain

The fractional ASA of the side chain atoms is computed by division of the sum of the ASA of the atoms in the side chain by a value representing the ASA of the side chain atoms of that residue type in an extended ALA-x-ALA tripeptide as described in Hubbard, Campbell & Thornton (1991) J. Mol. Biol. 220, 507–530. For this example the CA atom is regarded as a part of the side chain of glycine residues but not for the remaining residues. The following values are used as standard 100% ASA for the side chain:

| | |
|---|---|
| Ala | 69.23 Å$^2$ |
| Arg | 200.35 Å$^2$ |
| Asn | 106.25 Å$^2$ |
| Asp | 102.06 Å$^2$ |
| Cys | 96.69 Å$^2$ |
| Gln | 140.58 Å$^2$ |
| Glu | 134.61 Å$^2$ |
| Gly | 32.28 Å$^2$ |
| His | 147.00 Å$^2$ |
| Ile | 137.91 Å$^2$ |
| Leu | 140.76 Å$^2$ |
| Lys | 162.50 Å$^2$ |
| Met | 156.08 Å$^2$ |
| Phe | 163.90 Å$^2$ |
| Pro | 119.65 Å$^2$ |
| Ser | 78.16 Å$^2$ |
| Thr | 101.67 Å$^2$ |
| Trp | 210.89 Å$^2$ |
| Tyr | 176.61 Å$^2$ |
| Val | 114.14 Å$^2$ |

Residues not detected in the structure are defined as having 100% exposure as they are thought to reside in flexible regions.

Determining Distances Between Atoms

The distance between atoms is determined using molecular graphics software, e.g. InsightII v. 98.0, MSI Inc.

EXAMPLES

Example 1

Determination of Surface-Exposed Amino Acids

The coordinates for the X-ray structure of wild-type human APC (Mather, T., Oganessyan, V., Hof, P., Huber, R., Foundling, S., Esmon, C., Bode, W., 1996) are available from the Protein Data Bank (PDB) (Bernstein et. al. J. Mol. Biol. (1977) 112 pp. 535) and electronically available via The Research Collaboratory for Structural Bioinformatics PDB at www.pdb.org under accession code 1AUT. All water molecules as well as the covalently bound inhibitor were removed from the structure before the calculation of accessible surface area was done. In the present example the betahydroxy-ASP (AP) at position 71 is treated as a normal ASP residue. The residues K156–R169 (the Lys-Arg dipeptide and the activation peptide) were not included in the calculations.

Sequence Numbering

The sequence numbering used in this example is identical to the sequence numbering of the zymogen protein C having the amino acid sequence SEQ ID NO:4.

Surface Exposure

Performing fractional ASA calculations on the APC molecule resulted in the following residues having zero side chain accessibility: G67, C89, C98, G103, C105, H107, C109, Y124, G142, G173, V186, L187, A198, V199, I201, V206, L207, T208, A210, C212, V221, E235, I258, A259, L260, L261, L263, A267, V274, I276, L283, V297, C331, M335, A346, G361, M364, T371, F373, L374, G376, L377, V392, I403.

The following residues were found to have more than 25% of their side chain exposed to the surface: Q49, L51, V52, P54, L55, E56, H57, P58, C59, A60, S61, G65, H66, T68, I70, D71, G72, I73, G74, S75, F76, S77, D79, R81, S82, G83, W84, E85, R87, F88, Q90, R91, E92, F95, L96, N97, S99, L100, D101, L110, E111, E112, V113, G114, W115, R117, S119, P122, G123, K125, G127, D128, D129, L130, L131, Q132, H134, P135, A136, V137, K138, R143, W145, K146, D172, K174, M175, R177, R178, D180, D189, S190, K191, K192, K193, H202, P203, H211, D214, E215, S216, K217, K218, L220, R229, R230, W231, K233, W234, L236, D237, D239, K241, E242, V243, F244, V245, P247, N248, S250, K251, S252, T253, T254, D255, A264, Q265, P266, T268, S270, Q271, D280, S281, G282, E285, R286, E287, Q290, A291, G292, Q293, E294, L296, Y302, H303, S304, S305, R306, E307, K308, E309, G310, K311, R312, N313, R314, T315, F316, F320, K322, P327, H328, N329, E330, S332, H369, V334, S336, N337, M338, S340, E341, I348, L349, G350, D351, R352, E357, S367, H369, G370, E382, G383, C384, L386, L387, H388, R398, D401, H404, G405, H406, R408, D409. As it appears, the active site histidine (H211) was found to be surface exposed. H211 is, however, not a candidate for being modified according to the present invention. Furthermore, the cysteine residues listed above are normally not candidates for being modified according to the present invention.

The following residues were found to have more than 50% of their side chain exposed to the surface: Q49, L51, V52, P54, L55, E56, A60, S61, G65, I70, D71, G72, I73, G74, S75, S77, D79, R81, S82, R87, R91, E92, F95, L96, N97, S99, E111, V113, G114, W115, R117, P122, K125, D128, D129, L130, Q132, H134, V137, K138, K146, D172, K174, R177, S190, K191, K192, K193, D214, E215, K217, K218, R229, R230, W231, K233, D239, K241, E242, P247, N248, K251, S252, Q265, P266, T268, Q271, S281, E285, Q290, G292, Y302, S305, R306, E307, K308, E309, A310, R312, N313, T315, K322, N329, E330, E333, S336, N337, M338, E341, I348, G350, R352, E357, G370, G383, H388, R398, D401, H404, G405, R408, D409.

The residues A1, N2, S3, F4, L5, E6, E7, L8, R9, H10, S11, S12, L13, E14, R15, E16, C17, I18, E19, E20, I21, C22, D23, F24, E25, E26, A27, K28, E29, I30, F31, Q32, N33, V34, D35, D36, T37, L38, A39, F40, W41, S42, K43, H44, V45, D46, G47, D48, R147, M148, E149, K150, K151, R152, S153, H154, L155, K410, E411, A412, P413, Q414, K415, S416, W417, A418, P419 are not included in the structure and are, in the present application, regarded as being 100% exposed to the surface.

Example 2

Determination of Active Site Region

In determining the active site region the following approach was followed: By super-imposing the heavy chain of APC (1AUT) onto the X-ray structure of a ternary complex between Factor VIIa, Tissue Factor and a variant of BPTI bound in the active site (PDB accession code 1FAK. See Zhang, E., St Charles, R., Tulinsky, A.: Structure of Extracellular Tissue Factor Complexed with Factor Viia Inhibited with a Bpti Mutant *J. Mol. Biol.* 285 pp. 2089 (1999)) using the program Modeller '98 enabled the definition of the "active site region" as any residue in the APC heavy chain having an atom within a distance of 12Å from the superimposed BPTI molecule. Furthermore, from a visual inspection a loop just outside this region (residues 306–314) was also considered to constitute part of the active site region.

Using this approach the following amino acid residues were found to be included in the "active site region":

L170, I171, D172, G173, Q184, V185, V186, L187, L188, D189, S190, K191, K192, K193, L194, A195, C196, G197, A198, T208, A209, A210, H211, C212, M213, D214, E215, S216, K217, K218, L219, L220, L228, I240, V243, V245, N248, Y249, S250, K251, S252, T253, T254, D255, N256, D257, I258, A259, L261, T295, L296, V297, T298, G299, W300, G301, Y302, H303, S304, S305, R306, E307, K308, E309, A310, K311, R312, N313, R314, T315, F316, I321, I323, P324, V326, C331, V334, M335, S336, N337, M338, V339, M343, L344, C345, A346, G347, I348, L349, D351, R352, Q353, D354, A355, C356, E357, G358, D359, S360, G361, G362, P363, M364, G376, L377, V378, S379, W380, G381, E382, G383, C384, G385, L386, L387, H388, N389, Y390, G391, V392, Y393 and T394. Although listed here, the active site residues (H211, D257 and S360) are not candidates for being modified according to the present invention. Furthermore, the cysteine residues listed above are normally not candidates for being modified according to the present invention.

Example 3

Determination of Surface-Exposed Amino Acids within the Active Site Region

Combining the list of amino acids having more than 25% of their side chain exposed to the surface (from Example 1) with the list of amino acids included in the active site region (from Example 2), the following amino acid residues were found to be within the active site region and, at the same time, having at least 25% of its side chain exposed to the surface:

D172, D189, S190, K191, K92, K193, D214, E215, S216, K217, K218, H211L220, V243, V245, N248, S250, K251, S252, T253, T254, D255, L296, Y302, H303, S304, S305, R306, E307, K308, E309, A310, K311, R312, N313, R314, T315, F316, V334, S336, N337, M338, I348, L349, D351, R352, E357, E382, G383, C384, L386, L387 and H388. Although listed here, the active site histidine (H211) is not a candidate for being modified according to the present invention. Moreover, C384 is normally not a candidate for being modified according to the present invention.

Example 4

Construction of Protein C Expression Vector

A gene encoding the human protein C precursor was constructed by assembly of synthetic oligonucleotides by PCR using methods similar to the ones described in Stemmer et al. (1995) Gene 164, pp. 49–53. The native protein C signal sequence was maintained in order to allow secretion of the gene product. The synthetic gene was designed with a NheI site at the 5'-end and a XbaI site at the 3'-end and subcloned behind the CMV promoter in pcDNA3.1/Hygro (Invitrogen) using these sites. The protein C precursor sequence in the resulting plasmid, termed pCR4, is given in SEQ ID NO:1.

Furthermore, in order to test for a higher gene expression, the synthetic gene was cloned into the KpnI-XbaI sites of pcDNA3.1/Hygro containing an intron (from pCI-Neo (Promega)) in the 5' untranslated region of the gene. The resulting plasmid was termed pRC2.

Example 5

Site Directed Mutagenesis

All the mutants of protein C were constructed using Quick-Change (Stratagene). Primers were purchased from TAG Technology (Copenhagen) containing the appropriate mutations. The PCR reactions were performed according to the manufacturer's manual and the plasmids were transformed into TG1 competent cells. Plasmid preparations were made on single clones and the sequences were verified using a DNA sequencer 3100 genetic Analyser (ABI).

Primers:

```
D172N
POF003 (SEQ ID NO:5):
CAAGTAGATCCGCGGCTCATTAACGGGAAGATGACCAGGCGGGG
POF004 (SEQ ID NO:6):
CCCCGCCTGGTCATCTTCCCGTTAATGAGCCGCGGATCTACTTG

D214N
EKO001 (SEQ ID NO:7):
CTGACAGCGGCCCACTGCATGAACGAGTCCAAGAAGCTCCTTGTC
EKO002 (SEQ ID NO:8):
GACAAGGAGCTTCTTGGACTCGTTCATGCAGTGGGCCGCTGTCAG

D214A
EKO048 (SEQ ID NO:9):
CTGACAGCGGCCCACTGCATGGCCGAGTCCAAGAAGCTCCTTGTC
EKO049 (SEQ ID NO:10):
GACAAGGAGCTTCTTGGACTCGGCCATGCAGTGGGCCGCTGTCAG

K251N
EKO003 (SEQ ID NO:11):
CTTCGTCCACCCCAACTACAGCAACAGCACCACCGACAATGACATC
EKO004 (SEQ ID NO:12):
GATGTCATTGTCGGTGGTGCTGTTGCTGTAGTTGGGGTGGACGAAG

S252N
EKO005 (SEQ ID NO:13):
CGTCCACCCCAACTACAGCAAGAACACCAGCGACAATGACATCGC
EKO006 (SEQ ID NO:14):
GCGATGTCATTGTCGGTGGTGTTCTTGCTGTAGTTGGGGTGGACG

Y302N
EKO007 (SEQ ID NO:15):
CCCTCGTGACGGGCTGGGGCAACCACAGCAGCCGAGAGAAGGAGGCC
EKO008 (SEQ ID NO:16):
GGCCTCCTTCTCTCGGCTGCTGTGGTTGCCCCAGCCCGTCACGAGGG

M338N
EKO011 (SEQ ID NO:17):
CAGCGAGGTCATGAGCAACAACGTGTCTGAGAACATGC
EKO012 (SEQ ID NO:18):
GCATGTTCTCAGACACGTTGTTGCTCATGACCTCGCTG

M338A
EKO046 (SEQ ID NO:19):
GCAGCGAGGTCATGAGCAACGCCGTGTCTGAGAACATGC
EKO047 (SEQ ID NO:20):
GCATGTTCTCAGACACGGCGTTGCTCATGACCTCGCTGC

D189N+K191N
EKO019 (SEQ ID NO:21):
CCCCTGGCAGGTGGTCCTGCTGAACTCAAACAAGAAGCTGGCCTGCGGGG
EKO020 (SEQ ID NO:22):
CCCCGCAGGCCAGCTTCTTGTTTGAGTTCAGCAGGACCACCTGCCAGGGG

D189N+K191T
EKO033 (SEQ ID NO:23):
CCCCTGGCAGGTGGTCCTGCTGAACTCAACCAAGAAGCTGGCCTGCGGGG
EKO034 (SEQ ID NO:24):
CCCCGCAGGCCAGCTTCTTGGTTGAGTTCAGCAGGACCACCTGCC

S190N+K192T
EKO044 (SEQ ID NO:25):
GGCAGGTGGTCCTGCTGGACAACAAGACCAAGCTGGCCTGCGGGGCAGTGC
EKO045 (SEQ ID NO:26):
GCACTGCCCCGCAGGCCAGCTTGGTCTTGTTGTCCAGCAGGACCACCTGCC

K191N+K193T
EKO050 (SEQ ID NO:27):
GTCCTGCTGGACTCAAACAAGACCCTGGCCTGCGGGGCAGTG
EKO051 (SEQ ID NO:28):
CACTGCCCCGCAGGCCAGGGTCTTGTTTGAGTCCAGCAGGAC

K217N+L219T
EKO029 (SEQ ID NO:29):
GCATGGATGAGTCCAACAAGACCCTTGTCAGGCTTGGAGAGTATGACC
EKO030 (SEQ ID NO:30):
GGTCATACTCTCCAAGCCTGACAAGGGTCTTGTTGGACTCATCCATGC

T253N+D255T
EKO031 (SEQ ID NO:31):
CCAACTACAGCAAGAGCAACACCACCAATGACATCGCACTGCTGCACCTGGC
EKO032 (SEQ ID NO:32):
GCCAGGTGCAGCAGTGCGATGTCATTGGTGGTGTTGCTCTTGCTGTAGTTGG

S305N+E307T
EKO023 (SEQ ID NO:33):
GGCTGGGGCTACCACAGCAACCGAACCAAGGAGGCCAAGAGAAACCGC
EKO024 (SEQ ID NO:34):
GCGGTTTCTCTTGGCCTCCTTGGTTCGGTTGCTGTGGTAGCCCCAGCC

E307N+E309T
EKO025 (SEQ ID NO:35):
GGCTACCACAGCAGCCGAAACAAGACCGCCAAGAGAAACCGCACCTTCG
EKO026 (SEQ ID NO:36):
CGAAGGTGCGGTTTCTCTTGGCGGTCTTGTTTCGGCTGCTGTGGTAGCC

S336N+M338T
EKO027 (SEQ ID NO:37):
GCAGCGAGGTCATGAACAACACCGTGTCTGAGAACATGCTGTGTGCGGG
EKO028 (SEQ ID NO:38):
CCCGCACACAGCATGTTCTCAGACACGGTGTTGTTCATGACCTCGCTGC

L386N+H388T
EKO017 (SEQ ID NO:39):
GGTGAGCTGGGGTGAGGGCTGTGGGAACCTTACCAACTACGGCGTTTACACC
EKO018 (SEQ ID NO:40):
GGTGTAAACGCCGTAGTTGGTAAGGTTCCCACAGCCCTCACCCCAGCTCACC
```

Example 6

Production

Transient expression of wild-type protein C and protein C variants was performed using the Fugene transfection reagent (Roche) in COS 7 cells grown in DMEM (Gibco 21969-035) supplemented with 10% fetal serum, 2 mM L-glutamine, 100 U/ml of penicillin, 100 µg/ml streptomycin and 5 µg/ml vitamin K. On the day of transfection the medium was substituted with fresh medium 4–5 hours before transfection. The day after transfection the medium was substituted with serum-free production medium based on DMEM (Gibco 31053-028) supplemented with 2 mM L-glutamine, 1 mM Sodium Pyruvate, 1/500 Ex-cyte (serologicals) plemented with 2 mM L-glutamine, 1 mM Sodium Pyruvate, 1/500 Ex-cyte (serologicals) 1/100 ITSA (Gibco 51300-044), 100 U/ml of penicillin, 100 µg/ml streptomycin and 5 µg/ml vitamin K. After incubation for two days the medium was harvested and the expressed variants were analysed for production and activity (see Example 9 below).

Example 7

Purification

Approximately 15 mg Ca specific monoclonal antibody was coupled to 5 ml CNBr-activated Sepharose FF from Pharmacia according to the manufacturer's instructions. Approximately 1 ml of the coupled matrix was packed in a HR 10 column and washed with buffer A (20 mM Tris, 0.3 M NaCl, 5 mM $CaCl_2$, pH 7.5) at a flow rate of 1 ml/min. Approximately 90 ml of sterile filtered culture medium was made 0.3 M NaCl and 5 mM $CaCl_2$ and applied to the column at the same flow rate. Prior to elution, the column was washed with 20 column volumes of buffer A. Elution was carried out with buffer B (20 mM Tris and 10 mM EDTA, pH 7.5) and fractionated in 1 ml fractions. Fractions containing protein C, as judged by $OD_{280}$, western blot and SDS-PAGE, were pooled and stored at –80° C. The above-described purification procedure represents one out of several possible procedures for purifying protein C (see, for example, Kiesel, J. Clin. Invest. (1979) 64 pp. 761–769).

The purified proteins were activated using the activation protocol (see Example 8 below). The purity of all proteins was checked using polyacrylamide gel electrophoresis (PAGE) analysis. In addition, the degree of glycosylation was estimated from these gel analyses by monitoring changes in molecular weight. Increased apparent molecular weights compared to the wild-type human APC molecule demonstrate that the APC variants have been glycosylated.

An example of the wild-type APC and APC variants can be seen in FIG. 1. The proteins migrates on the gel as three dominate bands corresponding to the α- and β-bands of the heavy chain, with an apparent molecular weight of 41,000 and 37,000 respectively, and the light chain with an apparent molecular weight of 22,000. The degree of glycosylation was also investigated in the PAGE analysis. FIG. 1 includes two APC variants that are glycosylated in the introduced glycosylation site. The migration of the heavy chains of the APC variant D214N and M338N shifted to more cathodal positions, showing that these two variants are glycosylated and the site is fully used. From the examination of the mobility of the heavy chain subforms (α and β), it is evident that the molecular weight of the carbohydrate side chains at each site is about 3,000 to 4,000.

Example 8

Activation

The protein C variants and conjugates were activated using the venom protein C activator, ACC-C (Nakagaki et al., Thrombosis Research 58:593–602, 1990). The zymogen forms were incubated at 37° C. for about 60 min in 50 mM Tris-HCl (pH 7.5), 100 mM NaCl, 5 mM EDTA, using a final concentration of 1 ng/ml of ACC-C. The activation process was checked using the APC amidolytic activity assay (see example 9 below) and polyacrylamide gel electrophoresis analysis.

Example 9

Determination of Amidolytic Activity

APC Amidolytic Assay

The amidolytic activity of human APC and the compounds of the invention is determined using the peptide substrate SPECTROZYME PCa with the formula H-D-Lys (γ-Cbo)-Pro-Arg-pNA.2AcOH (American Diagnostica Inc, product # 336) at a final concentration of 0.5 mM. Assays are performed at 23° C. in 50 mM Tris-HCl (pH 8.3), 100 mM NaCl, 5 mM $CaCl_2$. The rate of hydrolysis of the PCa substrate by human APC and the compounds of the invention are recorded for 3 min at 405 nm as the change in absorbance units/min in a plate reader.

Results

All expressed and activated conjugates and variants were analysed for activity. 4 µl (unpurified) cell culture medium was assayed as described right above. The obtained activities, which do not reflect the specific activities since they depend inter alia on the expression level, indicate whether the proteins were expressed and whether they possessed activity.

The following activities were obtained:

TABLE 1a

| Compound | milliOD$_{405}$/min |
| --- | --- |
| wild-type COS 7 APC | 41 |
| D214N | 28 |
| D214A (control) | 10 |
| K251N* | 19 |
| S252N* | 16 |
| Y302N* | 14 |
| M338N | 53 |
| M338A (control) | 33 |
| D189N + K191T | 8 |
| D189N + K191N (control) | 12 |
| S190N + K192T* | 29 |
| K191N + K193T | 4 |
| K217 + L219T | 16 |
| T253N + D255T | 2 |
| S305N + E307T | 6 |
| E307N + E309T | 30 |
| S336N + M338T | 4 |
| L386N + H388T | 13 |

*No detectable sugar moiety attached to the introduced glycosylation site as judged from SDS-PAGE Selected candidates were purified and their specific amidolytic activities were measured in the above assay using a protein concentration of 30 nM. The following activities were found:

TABLE 1b

| Compound | milliOD$_{405}$/min | % of wild-type APC |
|---|---|---|
| wild-type COS 7 APC | 48.9 | — |
| D214N | 34.8 | 71 |
| K251N* | 45.2 | 92 |
| S252N* | 43.1 | 88 |
| M338N | 44.8 | 92 |
| S336N + M338T | 41.5 | 85 |
| L386N + H388T | 23.0 | 47 |

*No detectable sugar moiety attached to the introduced glycosylation site as judged from SDS-PAGE As it appears, the specific amidolytic activity of the tested conjugates and variants is at the same level as the wild-type human APC molecule.

Example 10

Determination of Anticoagulant Activity

APC Clotting Assay

Anticoagulant activity is assessed by monitoring the prolongation of clotting time in the activated partial thromboplastin time (APTT) assay using Nycoplastin (Nycomed, product no. 1002448) together with Normal Hemostasis Reference Plasma (American Diagnostica Inc., catalogue no. 258N). Coagulation is started by mixing the APTT reagent containing human APC or compounds of the invention with the normal hemostasis reference plasma at 37° C. and measuring the clotting time by manual mixing. The clotting time for the human APC is compared to the clotting time of the compounds of the invention to calculate the anticoagulant activity expressed in percentage to the human APC anticoagulant activity.

Results

Using the above assay the following anticoagulant activities were found:

TABLE 2

| Compound | Anticoagulant activity (% of human APC) |
|---|---|
| D214N | 22.4 |
| K251N* | 24.5 |
| S252N* | 24.5 |
| M338N | 34.7 |
| L386N + H388T | 14.3 |

*No detectable sugar moiety attached to the introduced glycosylation site as judged from SDS-PAGE These results show that the anticoagulant properties of the conjugates and variants of the invention are preserved to a large extent. This clearly shows that it is possible to design APC variants and conjugates with significantly increased resistance toward inhibition in plasma (see examples below) with retained anticoagulant activity.

Example 11

Inactivation by alpha-1-antitrypsin

Alpha-1-Antitrypsin Inactivation Assay

Human APC or compounds of the invention are incubated with 16.6 or 42.3 μM human alpha-1-antitrypsin (Sigma) in 10 mM Tris-HCl (pH 7.5), 150 mM NaCl, 5 mM CaCl$_2$ containing 0.1% BSA at 37° C. After 20 hours incubation a 15 μl sample of the incubated mixtures is added to 110 μl 50 mM Tris-HCl (pH 8.3), 100 mM NaCl, 5 mM CaCl$_2$ in microplates and assayed for APC amidolytic activity as described in the "APC Amidolytic Assay". The remaining activity is calculated by normalizing with the activity obtained in samples lacking alpha-1-antitrypsin but otherwise incubated under identical conditions.

Results

Using the above assay the following results were obtained:

TABLE 3

| | % residual amidolytic activity | |
|---|---|---|
| Compound | 16.6 μM inhibitor | 42.3 μM inhibitor |
| wild-type plasma APC | 10 | 2 |
| wild-type COS 7 APC | 7 | <1 |
| D214N | 80 | 81 |
| D214A (control) | 21 | 1 |
| K251N* | 62 | 53 |
| S252N* | 62 | 34 |
| Y302N* | 50 | 30 |
| M338N | 38 | 12 |
| M338A (control) | 9 | 2 |
| D189N + K191T | 90 | 77 |
| D189N + K191N (control) | 12 | <1 |
| S190N + K192T* | 28 | 5 |
| K191N + K193T | 59 | 24 |
| K217 + L219T | 20 | 4 |
| T253N + D255T | 56 | 38 |
| S305N + E307T | 42 | 9 |
| E307N + E309T | 10 | <1 |
| S336N + M338T | 72 | 40 |
| L386N + H388T | 68 | 44 |

Figure 2:
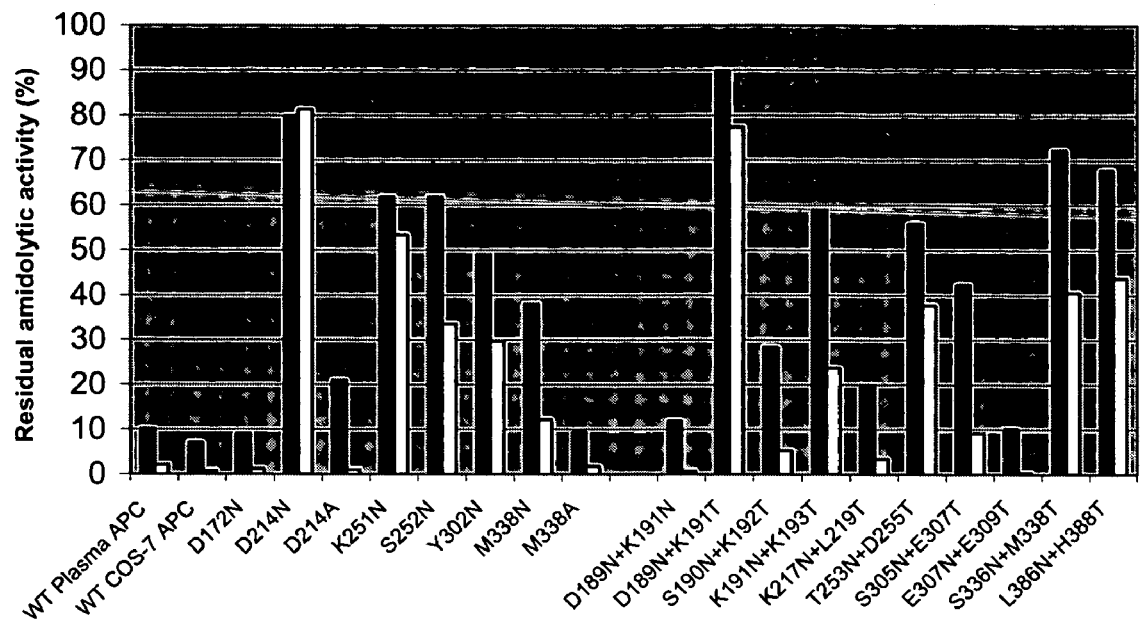
FIG. 2 shows the residual amidolytic activity of various conjugates and variants of the invention after incubation with different concentrations of alpha-1-antitrypsin (16.6 μM (black bars) and 42.3 μM (white bars)) for 20 hours at 37° C. Details are given in Example 11 herein.

*No detectable sugar moiety attached to the introduced glycosylation site as judged from SDS-PAGE The data are also shown in FIG. 2. The results show that practically all of the conjugates have increased resistance towards alpha-1-antitrypsin inhibition. In particular, D214N and D189N+K191T retain more than 70% of their amidolytic activity even at the highest alpha-1-antitrypsin concentration. The effect of the glycosylation of these compounds can be seen when comparing these two conjugates with D214A and D189N+K191N, which lack glycosylation. These variants are inhibited significantly more than their glycosylated equivalents indicating that glycosylation is important for improving the resistance towards alpha-1-antitrypsin inhibition. Moreover, it should be noted that the variants K251N, S252N, Y302N and S190N+K192T, which apparently have not utilized their introduced glycosylation site (as judged from SDS-PAGE), have significantly increased their resistance towards alpha-1-antitrypsin inhibition as compared to wild-type human APC.

Example 12

Inactivation by Human Plasma

Human Plasma Inactivation Assay I

Human APC or compounds of the invention are incubated in 90% normal human plasma (Sigma Diagnostics, Accuclot™ reference plasma) containing 50 mM Tris-HCl (pH 7.5), 100 mM NaCl, 5 mM CaCl$_2$ at 37° C. Aliquots are removed after 200 min and assayed for APC amidolytic activity as described in the "APC Amidolytic Assay". The residual APC activity after 200 min is expressed in percentage of the APC activity measured at the start of the experiment.

Results

Using the above assay the following results were obtained:

TABLE 4

| Compound | % residual amidolytic activity after 200 min in 90% normal human plasma |
|---|---|
| wild-type plasma APC | 5 |
| wild-type COS 7 APC | 7 |
| D214N | 80 |
| K251N* | 57 |
| S252N* | 45 |
| M338N | 22 |
| S336N + M338T | 45 |
| L336N + H388T | 72 |

*No detectable sugar moiety attached to the introduced glycosylation site as judged from SDS-PAGE The above results clearly indicated that the conjugates as well as the variants according to the invention are highly resistance towards inactivation in human plasma.

Example 13

In Vitro Half-Life in Human Plasma

Human Plasma Inactivation Assay II

Human APC or compounds of the invention are incubated in 90% normal human plasma (Sigma Diagnostics, Accu-clot™ reference plasma) containing 50 mM Tris-HCl (pH 7.5), 100 mM NaCl, 5 mM $CaCl_2$ at 37° C. Aliquots are removed at various time-points and assayed for APC amidolytic activity as described in the "APC Amidolytic Assay". The residual APC activity at the various time-points is expressed in percentage of the APC activity measured at the start of the experiment. The in vitro half-life (expressed in minutes) is calculated as the time at which 50% of the APC activity is still present.

Results

The following in vitro half-lives were obtained:

TABLE 5

| Compound | In vitro half-life (min) | Fold increase relative to wild-type human APC |
|---|---|---|
| wild-type plasma APC | 40 | — |
| wild-type COS 7 APC | 42 | — |
| D214N | >400 | >10 |
| K251N* | 255 | 6.4 |
| S252N* | 155 | 3.9 |
| M338N | 85 | 2.1 |
| S336N + M338T | 185 | 4.6 |
| L386N + H388T | >400 | >10 |

Figure 3:
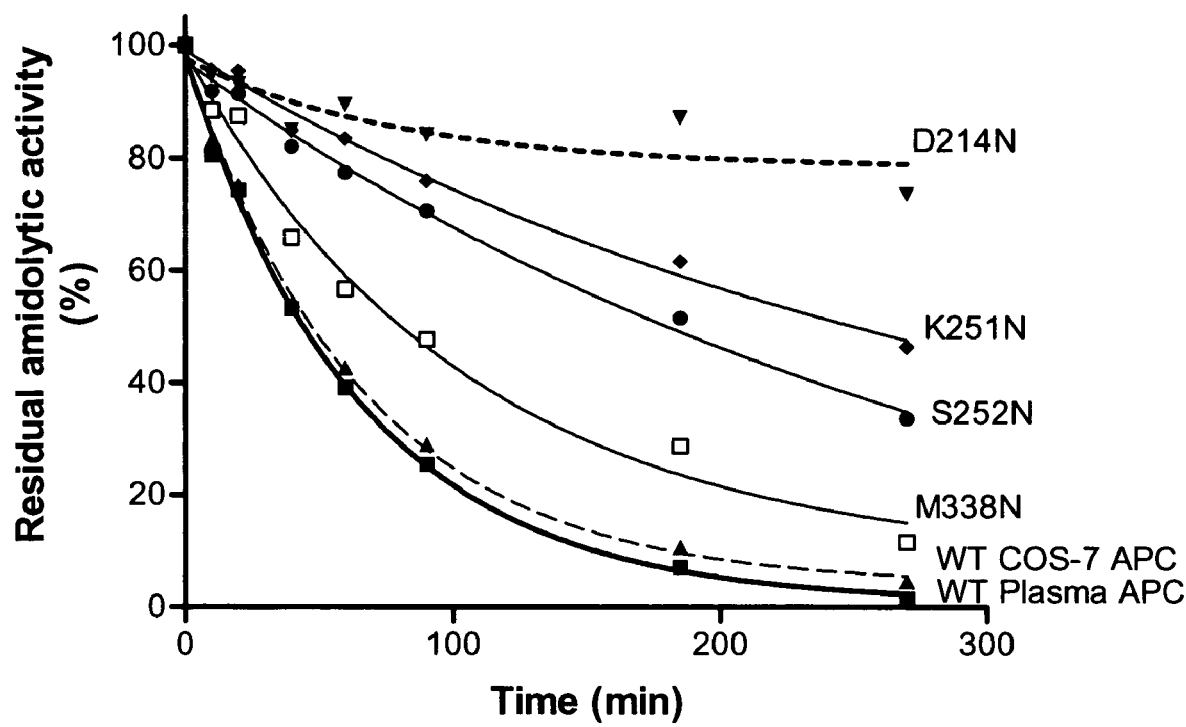
FIGS. 3 and 4 show the residual amidolytic activity of various conjugates and variants of the invention as a function of time in human plasma. Details, including the calculated in vitro half-lives in human plasma, are given in Example 13 herein.
Figure 4:
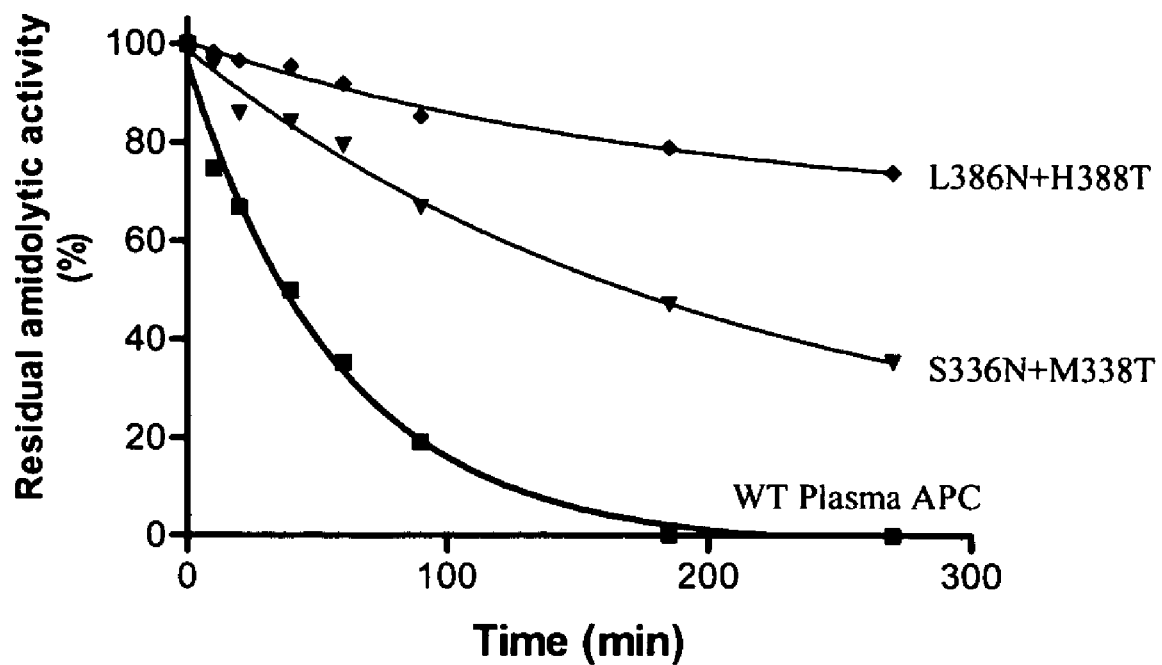

*No detectable sugar moiety attached to the introduced glycosylation site as judged from SDS-PAGE The experimental data points are shown in FIGS. 3 and 4. The results show that the APC variants and conjugates have significantly increased in vitro half-lives in human plasma. Especially the D214N and L386N+H388T conjugates show a significantly increased in vitro half-life (increased more than 10 times).

Example 14

Determination of Anti-Inflammatory Effect

APC Anti-Inflammatory Assay

The anti-inflammatory properties of the APC conjugates are investigated using recombinant tumor necrosis factor α (TNFα) (catalogue number: 210-TA, R&D Systems, Minneapolis, USA) stimulated human umbilical vein endothelial cells (HUVEC) (catalogue number: CC-2519, Clonetics, San Diego, USA). HUVEC is stimulated using 1 ng/ml TNFα for about 7 hours. Then, various concentrations (0–200 nM) of human APC and the APC conjugates are incubated for up to 20 hours. The cells are removed by trypsination and analysed using flow cytometry measuring the surface expression of ICAM-1, VCAM-1 and/or E-selecting. For E-selecting quantification a FITC-conjugated anti-human E-selecting monoclonal antibody (CD62E) (catalog number: BBA21, R&D Systems, Minneapolis, USA) is used. The anti-inflammatory effect of human APC and the APC conjugates is determined by calculating the APC concentration needed to suppress the TNFα stimulation of E-selecting to 50% compared to the effect of TNFα obtained without APC. This APC concentration is used to indicate the half maximum inhibitory concentration ($IC_{50}$), and these values are determined for human APC and each individual APC conjugate.

While the foregoing invention has been described in some detail for purposes of clarity and understanding, it will be clear to one skilled in the art from a reading of this disclosure that various changes in form and detail can be made without departing from the true scope of the invention. It is understood that the examples and embodiments described herein are for illustrative purposes only and that various modifications or changes in light thereof will be suggested to persons skilled in the art and are to be included within the spirit and purview of this application and scope of the appended claims. For example, all the techniques and apparatus described above may be used in various combinations. All publications, patents, patent applications, and/or other documents cited in this application are incorporated herein by reference in their entirety for all purposes to the same extent as if each individual publication, patent, patent application, and/or other document were individually indicated to be incorporated herein by reference in its entirety for all purposes.

The invention claimed is:

1. A variant of a parent human protein C polypeptide, the variant comprising a sequence which
   (a) differs from the parent human protein C polypeptide sequence SEQ ID NO:4 in 1 to 15 amino acid residues, and
   (b) wherein the Asp residue at position 214 is substituted by an amino acid residue having a polar side chain or by an amino acid residue having an opposite charge to Asp,
   wherein the variant in activated form exhibits an amidolytic activity.

2. The variant of claim 1, wherein the activated form exhibits at least 10% of the amidolytic activity of human activated protein C (APC) when tested in the APC Amidolytic Assay.

3. The variant of claim 1 in activated form.

4. The variant of claim 1, wherein the amino acid residue having a polar side chain is selected from the group consisting of Sew, Thr, Cys, Tyr, Asn and Gln.

5. The variant of claim 4, comprising the substitution D214N or D214Q.

6. The variant of claim 1, wherein the amino acid residue having an opposite charge to Asp is selected from the group consisting of Lys and Arg.

7. The variant of claim 6, comprising the substitution D214K.

8. The variant of claim 1, wherein the variant in activated form exhibits about 5–75% of the anticoagulant activity of human APC when tested in the APC Clotting Assay.

9. The variant of claim 1, wherein the variant in activated form exhibits an increased resistance towards inactivation by alpha-1-antitrypsin as compared to human APC.

10. The variant of claim 1, wherein the variant in activated form exhibits an increased resistance towards inactivation by human plasma as compared to human APC.

11. The variant of claim 1, wherein rite variant in activated form has an increased functional in vivo half-life or an increased serum half-life as compared to human APC.

12. The variant of claim 1, wherein the sequence of the variant differs from the parent human protein C polypeptide sequence in 1 to 10 amino acid residues.

13. The variant of claim 1, which is in vivo glycosylated.

14. The variant of claim 1, further comprising a substitution in position 251.

15. The variant of claim 14, comprising the substitution K251D or K251N.

16. A pharmaceutical composition comprising the variant of claim 1 and at least one pharmaceutically acceptable carder or excipient.

* * * * *

UNITED STATES PATENT AND TRADEMARK OFFICE
CERTIFICATE OF CORRECTION

| | | |
|---|---|---|
| PATENT NO. | : 7,226,999 B2 | Page 1 of 1 |
| APPLICATION NO. | : 11/004111 | |
| DATED | : June 5, 2007 | |
| INVENTOR(S) | : Kim Vilbour Andersen et al. | |

It is certified that error appears in the above-identified patent and that said Letters Patent is hereby corrected as shown below:

Column 77, line 43, delete "Sew" and insert --Ser--.

Column 78, line 33, delete "rite" and insert --the--.

Column 78, line 47, delete "carder" and insert --carrier--.

Signed and Sealed this

Fourth Day of September, 2007

JON W. DUDAS
*Director of the United States Patent and Trademark Office*

SEQUENCE LISTING

<160> NUMBER OF SEQ ID NOS: 48

<210> SEQ ID NO 1
<211> LENGTH: 1383
<212> TYPE: DNA
<213> ORGANISM: Homo sapiens

```
<220> FEATURE:
<221> NAME/KEY: CDS
<222> LOCATION: (1)..(1383)
<220> FEATURE:
<221> NAME/KEY: sig_peptide
<222> LOCATION: (1)...(126)
<220> FEATURE:
<221> NAME/KEY: mat_peptide
<222> LOCATION: (127)..(1383)

<400> SEQUENCE: 1
```

| | | | | | | | | | | | | | | | | |
|---|---|---|---|---|---|---|---|---|---|---|---|---|---|---|---|---|
| atg | tgg | cag | ctc | aca | agc | ctc | ctg | ctg | ttc | gtg | gcc | acc | tgg | gga | att | 48 |
| Met | Trp | Gln | Leu | Thr | Ser | Leu | Leu | Leu | Phe | Val | Ala | Thr | Trp | Gly | Ile | |
| | -40 | | | | -35 | | | | | -30 | | | | | | |
| tcc | ggc | aca | cca | gct | cct | ctt | gac | tca | gtg | ttc | tcc | agc | agc | gag | cgt | 96 |
| Ser | Gly | Thr | Pro | Ala | Pro | Leu | Asp | Ser | Val | Phe | Ser | Ser | Ser | Glu | Arg | |
| | -25 | | | | | -20 | | | | | -15 | | | | | |
| gcc | cac | cag | gtg | ctg | cgg | atc | cgc | aaa | cgt | gcc | aac | tcc | ttc | ctg | gag | 144 |
| Ala | His | Gln | Val | Leu | Arg | Ile | Arg | Lys | Arg | Ala | Asn | Ser | Phe | Leu | Glu | |
| -10 | | | | | -5 | | | | -1 | 1 | | | | 5 | | |
| gag | ctc | cgt | cac | agc | agc | ctg | gag | cgg | gag | tgc | ata | gag | gag | atc | tgt | 192 |
| Glu | Leu | Arg | His | Ser | Ser | Leu | Glu | Arg | Glu | Cys | Ile | Glu | Glu | Ile | Cys | |
| | | | 10 | | | | | 15 | | | | | 20 | | | |
| gac | ttc | gag | gag | gcc | aag | gaa | att | ttc | caa | aat | gtg | gat | gac | aca | ctg | 240 |
| Asp | Phe | Glu | Glu | Ala | Lys | Glu | Ile | Phe | Gln | Asn | Val | Asp | Asp | Thr | Leu | |
| | | 25 | | | | | 30 | | | | | 35 | | | | |
| gcc | ttc | tgg | tcc | aag | cac | gtc | gac | ggt | gac | cag | tgc | ttg | gtc | ttg | ccc | 288 |
| Ala | Phe | Trp | Ser | Lys | His | Val | Asp | Gly | Asp | Gln | Cys | Leu | Val | Leu | Pro | |
| | 40 | | | | | 45 | | | | | 50 | | | | | |
| ttg | gag | cac | ccg | tgc | gcc | agc | ctg | tgc | tgc | ggg | cac | ggc | acg | tgc | atc | 336 |
| Leu | Glu | His | Pro | Cys | Ala | Ser | Leu | Cys | Cys | Gly | His | Gly | Thr | Cys | Ile | |
| 55 | | | | 60 | | | | | 65 | | | | | 70 | | |
| gac | ggc | atc | ggc | agc | ttc | agc | tgc | gac | tgc | cgc | agc | ggc | tgg | gag | ggc | 384 |
| Asp | Gly | Ile | Gly | Ser | Phe | Ser | Cys | Asp | Cys | Arg | Ser | Gly | Trp | Glu | Gly | |
| | | | 75 | | | | | 80 | | | | | 85 | | | |
| cgc | ttc | tgc | cag | cgc | gag | gtg | agc | ttc | ctc | aat | tgc | tcg | ctg | gac | aac | 432 |
| Arg | Phe | Cys | Gln | Arg | Glu | Val | Ser | Phe | Leu | Asn | Cys | Ser | Leu | Asp | Asn | |
| | | 90 | | | | | 95 | | | | | 100 | | | | |
| ggc | ggc | tgc | acg | cat | tac | tgc | cta | gag | gag | gtg | ggc | tgg | cgg | cgc | tgt | 480 |
| Gly | Gly | Cys | Thr | His | Tyr | Cys | Leu | Glu | Glu | Val | Gly | Trp | Arg | Arg | Cys | |
| | 105 | | | | | 110 | | | | | 115 | | | | | |
| agc | tgt | gcg | cct | ggc | tac | aag | ctg | ggg | gac | gac | ctc | ctg | cag | tgt | cac | 528 |
| Ser | Cys | Ala | Pro | Gly | Tyr | Lys | Leu | Gly | Asp | Asp | Leu | Leu | Gln | Cys | His | |
| 120 | | | | | 125 | | | | | 130 | | | | | | |
| ccc | gca | gtg | aag | ttc | cct | tgt | ggg | agg | ccc | tgg | aag | cgg | atg | gag | aag | 576 |
| Pro | Ala | Val | Lys | Phe | Pro | Cys | Gly | Arg | Pro | Trp | Lys | Arg | Met | Glu | Lys | |
| 135 | | | | 140 | | | | | 145 | | | | | 150 | | |
| aag | cgc | agt | cac | ctg | aaa | cga | gac | aca | gaa | gac | caa | gaa | gac | caa | gta | 624 |
| Lys | Arg | Ser | His | Leu | Lys | Arg | Asp | Thr | Glu | Asp | Gln | Glu | Asp | Gln | Val | |
| | | | 155 | | | | | 160 | | | | | 165 | | | |
| gat | ccg | cgg | ctc | att | gat | ggg | aag | atg | acc | agg | cgg | gga | gac | agc | ccc | 672 |
| Asp | Pro | Arg | Leu | Ile | Asp | Gly | Lys | Met | Thr | Arg | Arg | Gly | Asp | Ser | Pro | |
| | | 170 | | | | | 175 | | | | | 180 | | | | |
| tgg | cag | gtg | gtc | ctg | ctg | gac | tca | aag | aag | aag | ctg | gcc | tgc | ggg | gca | 720 |
| Trp | Gln | Val | Val | Leu | Leu | Asp | Ser | Lys | Lys | Lys | Leu | Ala | Cys | Gly | Ala | |
| | 185 | | | | | 190 | | | | | 195 | | | | | |
| gtg | ctc | atc | cac | ccc | tcc | tgg | gtg | ctg | aca | gcg | gcc | cac | tgc | atg | gat | 768 |
| Val | Leu | Ile | His | Pro | Ser | Trp | Val | Leu | Thr | Ala | Ala | His | Cys | Met | Asp | |
| | 200 | | | | | 205 | | | | | 210 | | | | | |
| gag | tcc | aag | aag | ctc | ctt | gtc | agg | ctt | gga | gag | tat | gac | ctg | cgg | cgc | 816 |
| Glu | Ser | Lys | Lys | Leu | Leu | Val | Arg | Leu | Gly | Glu | Tyr | Asp | Leu | Arg | Arg | |
| 215 | | | | 220 | | | | | 225 | | | | | 230 | | |

```
tgg gag aag tgg gag ctg gac ctg gac atc aag gag gtc ttc gtc cac        864
Trp Glu Lys Trp Glu Leu Asp Leu Asp Ile Lys Glu Val Phe Val His
            235                 240                 245 ccc aac tac agc aag agc acc acc gac aat gac atc gca ctg ctg cac        912
Pro Asn Tyr Ser Lys Ser Thr Thr Asp Asn Asp Ile Ala Leu Leu His
            250                 255                 260 ctg gcc cag ccc gcc acc ctc tcg cag acc ata gtg ccc atc tgc ctc        960
Leu Ala Gln Pro Ala Thr Leu Ser Gln Thr Ile Val Pro Ile Cys Leu
            265                 270                 275 ccg gac agc ggc ctt gca gag cgc gag ctc aat cag gcc ggc cag gag       1008
Pro Asp Ser Gly Leu Ala Glu Arg Glu Leu Asn Gln Ala Gly Gln Glu
        280                 285                 290 acc ctc gtg acg ggc tgg ggc tac cac agc agc cga gag aag gag gcc       1056
Thr Leu Val Thr Gly Trp Gly Tyr His Ser Ser Arg Glu Lys Glu Ala
295                 300                 305                 310 aag aga aac cgc acc ttc gtc ctc aac ttc atc aag att ccc gtg gtc       1104
Lys Arg Asn Arg Thr Phe Val Leu Asn Phe Ile Lys Ile Pro Val Val
                315                 320                 325 ccg cac aat gag tgc agc gag gtc atg agc aac atg gtg tct gag aac       1152
Pro His Asn Glu Cys Ser Glu Val Met Ser Asn Met Val Ser Glu Asn
            330                 335                 340 atg ctg tgt gcg ggc atc ctc ggg gac cgg cag gat gcc tgc gag ggc       1200
Met Leu Cys Ala Gly Ile Leu Gly Asp Arg Gln Asp Ala Cys Glu Gly
            345                 350                 355 gac agt ggg ggg ccc atg gtc gcc tcc ttc cac ggc acc tgg ttc ctg       1248
Asp Ser Gly Gly Pro Met Val Ala Ser Phe His Gly Thr Trp Phe Leu
        360                 365                 370 gtg ggc ctg gtg agc tgg ggt gag ggc tgt ggg ctc ctt cac aac tac       1296
Val Gly Leu Val Ser Trp Gly Glu Gly Cys Gly Leu Leu His Asn Tyr
375                 380                 385                 390 ggc gtt tac acc aaa gtc agc cgc tac ctc gac tgg atc cat ggg cac       1344
Gly Val Tyr Thr Lys Val Ser Arg Tyr Leu Asp Trp Ile His Gly His
                395                 400                 405 atc aga gac aag gaa gcc ccc cag aag agc tgg gca cct                   1383
Ile Arg Asp Lys Glu Ala Pro Gln Lys Ser Trp Ala Pro
            410                 415

<210> SEQ ID NO 2
<211> LENGTH: 461
<212> TYPE: PRT
<213> ORGANISM: Homo sapiens
<220> FEATURE:
<221> NAME/KEY: SIGNAL
<222> LOCATION: (1)...(42)
<220> FEATURE:
<221> NAME/KEY: CHAIN
<222> LOCATION: (43)...(461)

<400> SEQUENCE: 2

Met Trp Gln Leu Thr Ser Leu Leu Phe Val Ala Thr Trp Gly Ile
        -40                 -35                 -30

Ser Gly Thr Pro Ala Pro Leu Asp Ser Val Phe Ser Ser Glu Arg
    -25                 -20                 -15

Ala His Gln Val Leu Arg Ile Arg Lys Arg Ala Asn Ser Phe Leu Glu
-10                  -5                  -1   1                   5

Glu Leu Arg His Ser Ser Leu Glu Arg Glu Cys Ile Glu Glu Ile Cys
                10                  15                  20

Asp Phe Glu Glu Ala Lys Glu Ile Phe Gln Asn Val Asp Asp Thr Leu
            25                  30                  35

Ala Phe Trp Ser Lys His Val Asp Gly Asp Gln Cys Leu Val Leu Pro
```

```
                 40                  45                  50
Leu Glu His Pro Cys Ala Ser Leu Cys Cys His Gly Thr Cys Ile
 55                  60                  65                  70

Asp Gly Ile Gly Ser Phe Ser Cys Asp Cys Arg Ser Gly Trp Glu Gly
                 75                  80                  85

Arg Phe Cys Gln Arg Glu Val Ser Phe Leu Asn Cys Ser Leu Asp Asn
                 90                  95                 100

Gly Gly Cys Thr His Tyr Cys Leu Glu Val Gly Trp Arg Arg Cys
                105                 110                 115

Ser Cys Ala Pro Gly Tyr Lys Leu Gly Asp Asp Leu Leu Gln Cys His
            120                 125                 130

Pro Ala Val Lys Phe Pro Cys Gly Arg Pro Trp Lys Arg Met Glu Lys
135                 140                 145                 150

Lys Arg Ser His Leu Lys Arg Asp Thr Glu Asp Gln Glu Asp Gln Val
                155                 160                 165

Asp Pro Arg Leu Ile Asp Gly Lys Met Thr Arg Arg Gly Asp Ser Pro
                170                 175                 180

Trp Gln Val Val Leu Leu Asp Ser Lys Lys Lys Leu Ala Cys Gly Ala
            185                 190                 195

Val Leu Ile His Pro Ser Trp Val Leu Thr Ala Ala His Cys Met Asp
    200                 205                 210

Glu Ser Lys Lys Leu Leu Val Arg Leu Gly Glu Tyr Asp Leu Arg Arg
215                 220                 225                 230

Trp Glu Lys Trp Glu Leu Asp Leu Asp Ile Lys Glu Val Phe Val His
                235                 240                 245

Pro Asn Tyr Ser Lys Ser Thr Thr Asp Asn Asp Ile Ala Leu Leu His
                250                 255                 260

Leu Ala Gln Pro Ala Thr Leu Ser Gln Thr Ile Val Pro Ile Cys Leu
            265                 270                 275

Pro Asp Ser Gly Leu Ala Glu Arg Glu Leu Asn Gln Ala Gly Gln Glu
    280                 285                 290

Thr Leu Val Thr Gly Trp Gly Tyr His Ser Ser Arg Glu Lys Glu Ala
295                 300                 305                 310

Lys Arg Asn Arg Thr Phe Val Leu Asn Phe Ile Lys Ile Pro Val Val
                315                 320                 325

Pro His Asn Glu Cys Ser Glu Val Met Ser Asn Met Val Ser Glu Asn
                330                 335                 340

Met Leu Cys Ala Gly Ile Leu Gly Asp Arg Gln Asp Ala Cys Glu Gly
            345                 350                 355

Asp Ser Gly Gly Pro Met Val Ala Ser Phe His Gly Thr Trp Phe Leu
    360                 365                 370

Val Gly Leu Val Ser Trp Gly Glu Gly Cys Gly Leu Leu His Asn Tyr
375                 380                 385                 390

Gly Val Tyr Thr Lys Val Ser Arg Tyr Leu Asp Trp Ile His Gly His
                395                 400                 405

Ile Arg Asp Lys Glu Ala Pro Gln Lys Ser Trp Ala Pro
            410                 415
```

<210> SEQ ID NO 3
<211> LENGTH: 1257
<212> TYPE: DNA
<213> ORGANISM: Homo sapiens
<220> FEATURE:
<221> NAME/KEY: CDS
<222> LOCATION: (1)..(1257)

<400> SEQUENCE: 3

| | | | | | | | | | | | | | | | | |
|---|---|---|---|---|---|---|---|---|---|---|---|---|---|---|---|---|
| gcc | aac | tcc | ttc | ctg | gag | gag | ctc | cgt | cac | agc | agc | ctg | gag | cgg | gag | 48 |
| Ala | Asn | Ser | Phe | Leu | Glu | Glu | Leu | Arg | His | Ser | Ser | Leu | Glu | Arg | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tgc | ata | gag | gag | atc | tgt | gac | ttc | gag | gag | gcc | aag | gaa | att | ttc | caa | 96 |
| Cys | Ile | Glu | Glu | Ile | Cys | Asp | Phe | Glu | Glu | Ala | Lys | Glu | Ile | Phe | Gln | |
| | | 20 | | | | | 25 | | | | | 30 | | | | |

| | | | | | | | | | | | | | | | | |
|---|---|---|---|---|---|---|---|---|---|---|---|---|---|---|---|---|
| aat | gtg | gat | gac | aca | ctg | gcc | ttc | tgg | tcc | aag | cac | gtc | gac | ggt | gac | 144 |
| Asn | Val | Asp | Asp | Thr | Leu | Ala | Phe | Trp | Ser | Lys | His | Val | Asp | Gly | Asp | |
| | | 35 | | | | | 40 | | | | | 45 | | | | |

| | | | | | | | | | | | | | | | | |
|---|---|---|---|---|---|---|---|---|---|---|---|---|---|---|---|---|
| cag | tgc | ttg | gtc | ttg | ccc | ttg | gag | cac | ccg | tgc | gcc | agc | ctg | tgc | tgc | 192 |
| Gln | Cys | Leu | Val | Leu | Pro | Leu | Glu | His | Pro | Cys | Ala | Ser | Leu | Cys | Cys | |
| 50 | | | | | 55 | | | | | 60 | | | | | | |

| | | | | | | | | | | | | | | | | |
|---|---|---|---|---|---|---|---|---|---|---|---|---|---|---|---|---|
| ggg | cac | ggc | acg | tgc | atc | gac | ggc | atc | ggc | agc | ttc | agc | tgc | gac | tgc | 240 |
| Gly | His | Gly | Thr | Cys | Ile | Asp | Gly | Ile | Gly | Ser | Phe | Ser | Cys | Asp | Cys | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| cgc | agc | ggc | tgg | gag | ggc | cgc | ttc | tgc | cag | cgc | gag | gtg | agc | ttc | ctc | 288 |
| Arg | Ser | Gly | Trp | Glu | Gly | Arg | Phe | Cys | Gln | Arg | Glu | Val | Ser | Phe | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| aat | tgc | tcg | ctg | gac | aac | ggc | ggc | tgc | acg | cat | tac | tgc | cta | gag | gag | 336 |
| Asn | Cys | Ser | Leu | Asp | Asn | Gly | Gly | Cys | Thr | His | Tyr | Cys | Leu | Glu | Glu | |
| | | 100 | | | | | 105 | | | | | 110 | | | | |

| | | | | | | | | | | | | | | | | |
|---|---|---|---|---|---|---|---|---|---|---|---|---|---|---|---|---|
| gtg | ggc | tgg | cgg | cgc | tgt | agc | tgt | gcg | cct | ggc | tac | aag | ctg | ggg | gac | 384 |
| Val | Gly | Trp | Arg | Arg | Cys | Ser | Cys | Ala | Pro | Gly | Tyr | Lys | Leu | Gly | Asp | |
| | | 115 | | | | | 120 | | | | | 125 | | | | |

| | | | | | | | | | | | | | | | | |
|---|---|---|---|---|---|---|---|---|---|---|---|---|---|---|---|---|
| gac | ctc | ctg | cag | tgt | cac | ccc | gca | gtg | aag | ttc | cct | tgt | ggg | agg | ccc | 432 |
| Asp | Leu | Leu | Gln | Cys | His | Pro | Ala | Val | Lys | Phe | Pro | Cys | Gly | Arg | Pro | |
| 130 | | | | | 135 | | | | | 140 | | | | | | |

| | | | | | | | | | | | | | | | | |
|---|---|---|---|---|---|---|---|---|---|---|---|---|---|---|---|---|
| tgg | aag | cgg | atg | gag | aag | aag | cgc | agt | cac | ctg | aaa | cga | gac | aca | gaa | 480 |
| Trp | Lys | Arg | Met | Glu | Lys | Lys | Arg | Ser | His | Leu | Lys | Arg | Asp | Thr | Glu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gac | caa | gaa | gac | caa | gta | gat | ccg | cgg | ctc | att | gat | ggg | aag | atg | acc | 528 |
| Asp | Gln | Glu | Asp | Gln | Val | Asp | Pro | Arg | Leu | Ile | Asp | Gly | Lys | Met | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| agg | cgg | gga | gac | agc | ccc | tgg | cag | gtg | gtc | ctg | ctg | gac | tca | aag | aag | 576 |
| Arg | Arg | Gly | Asp | Ser | Pro | Trp | Gln | Val | Val | Leu | Leu | Asp | Ser | Lys | Lys | |
| | | 180 | | | | | 185 | | | | | 190 | | | | |

| | | | | | | | | | | | | | | | | |
|---|---|---|---|---|---|---|---|---|---|---|---|---|---|---|---|---|
| aag | ctg | gcc | tgc | ggg | gca | gtg | ctc | atc | cac | ccc | tcc | tgg | gtg | ctg | aca | 624 |
| Lys | Leu | Ala | Cys | Gly | Ala | Val | Leu | Ile | His | Pro | Ser | Trp | Val | Leu | Thr | |
| | | 195 | | | | | 200 | | | | | 205 | | | | |

| | | | | | | | | | | | | | | | | |
|---|---|---|---|---|---|---|---|---|---|---|---|---|---|---|---|---|
| gcg | gcc | cac | tgc | atg | gat | gag | tcc | aag | aag | ctc | ctt | gtc | agg | ctt | gga | 672 |
| Ala | Ala | His | Cys | Met | Asp | Glu | Ser | Lys | Lys | Leu | Leu | Val | Arg | Leu | Gly | |
| | | 210 | | | | | 215 | | | | | 220 | | | | |

| | | | | | | | | | | | | | | | | |
|---|---|---|---|---|---|---|---|---|---|---|---|---|---|---|---|---|
| gag | tat | gac | ctg | cgg | cgc | tgg | gag | aag | tgg | gag | ctg | gac | ctg | gac | atc | 720 |
| Glu | Tyr | Asp | Leu | Arg | Arg | Trp | Glu | Lys | Trp | Glu | Leu | Asp | Leu | Asp | Ile | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aag | gag | gtc | ttc | gtc | cac | ccc | aac | tac | agc | aag | agc | acc | acc | gac | aat | 768 |
| Lys | Glu | Val | Phe | Val | His | Pro | Asn | Tyr | Ser | Lys | Ser | Thr | Thr | Asp | Asn | |
| | | | | 245 | | | | | 250 | | | | | 255 | | |

| | | | | | | | | | | | | | | | | |
|---|---|---|---|---|---|---|---|---|---|---|---|---|---|---|---|---|
| gac | atc | gca | ctg | ctg | cac | ctg | gcc | cag | ccc | gcc | acc | ctc | tcg | cag | acc | 816 |
| Asp | Ile | Ala | Leu | Leu | His | Leu | Ala | Gln | Pro | Ala | Thr | Leu | Ser | Gln | Thr | |
| | | 260 | | | | | 265 | | | | | 270 | | | | |

| | | | | | | | | | | | | | | | | |
|---|---|---|---|---|---|---|---|---|---|---|---|---|---|---|---|---|
| ata | gtg | ccc | atc | tgc | ctc | ccg | gac | agc | ggc | ctt | gca | gag | cgc | gag | ctc | 864 |
| Ile | Val | Pro | Ile | Cys | Leu | Pro | Asp | Ser | Gly | Leu | Ala | Glu | Arg | Glu | Leu | |
| | | 275 | | | | | 280 | | | | | 285 | | | | |

| | | | | | | | | | | | | | | | | |
|---|---|---|---|---|---|---|---|---|---|---|---|---|---|---|---|---|
| aat | cag | gcc | ggc | cag | gag | acc | ctc | gtg | acg | ggc | tgg | ggc | tac | cac | agc | 912 |
| Asn | Gln | Ala | Gly | Gln | Glu | Thr | Leu | Val | Thr | Gly | Trp | Gly | Tyr | His | Ser | |
| 290 | | | | | 295 | | | | | 300 | | | | | | |

-continued

| | | |
|---|---|---|
| agc cga gag aag gag gcc aag aga aac cgc acc ttc gtc ctc aac ttc<br>Ser Arg Glu Lys Glu Ala Lys Arg Asn Arg Thr Phe Val Leu Asn Phe<br>305                        310                         315                     320 | 960 |
| atc aag att ccc gtg gtc ccg cac aat gag tgc agc gag gtc atg agc<br>Ile Lys Ile Pro Val Val Pro His Asn Glu Cys Ser Glu Val Met Ser<br>                     325                         330                     335 | 1008 |
| aac atg gtg tct gag aac atg ctg tgt gcg ggc atc ctc ggg gac cgg<br>Asn Met Val Ser Glu Asn Met Leu Cys Ala Gly Ile Leu Gly Asp Arg<br>        340                     345                     350 | 1056 |
| cag gat gcc tgc gag ggc gac agt ggg ggg ccc atg gtc gcc tcc ttc<br>Gln Asp Ala Cys Glu Gly Asp Ser Gly Gly Pro Met Val Ala Ser Phe<br>            355                     360                     365 | 1104 |
| cac ggc acc tgg ttc ctg gtg ggc ctg gtg agc tgg ggt gag ggc tgt<br>His Gly Thr Trp Phe Leu Val Gly Leu Val Ser Trp Gly Glu Gly Cys<br>370                        375                         380 | 1152 |
| ggg ctc ctt cac aac tac ggc gtt tac acc aaa gtc agc cgc tac ctc<br>Gly Leu Leu His Asn Tyr Gly Val Tyr Thr Lys Val Ser Arg Tyr Leu<br>385                        390                         395                   400 | 1200 |
| gac tgg atc cat ggg cac atc aga gac aag gaa gcc ccc cag aag agc<br>Asp Trp Ile His Gly His Ile Arg Asp Lys Glu Ala Pro Gln Lys Ser<br>                           405                         410                     415 | 1248 |
| tgg gca cct<br>Trp Ala Pro | 1257 |

<210> SEQ ID NO 4
<211> LENGTH: 419
<212> TYPE: PRT
<213> ORGANISM: Homo sapiens

<400> SEQUENCE: 4

Ala Asn Ser Phe Leu Glu Glu Leu Arg His Ser Ser Leu Glu Arg Glu
1                 5                   10                 15

Cys Ile Glu Glu Ile Cys Asp Phe Glu Glu Ala Lys Glu Ile Phe Gln
                   20                   25                   30

Asn Val Asp Asp Thr Leu Ala Phe Trp Ser Lys His Val Asp Gly Asp
                35                   40                   45

Gln Cys Leu Val Leu Pro Leu Glu His Pro Cys Ala Ser Leu Cys Cys
           50                   55                   60

Gly His Gly Thr Cys Ile Asp Gly Ile Gly Ser Phe Ser Cys Asp Cys
65                70                   75                   80

Arg Ser Gly Trp Glu Gly Arg Phe Cys Gln Arg Glu Val Ser Phe Leu
                85                   90                   95

Asn Cys Ser Leu Asp Asn Gly Gly Cys Thr His Tyr Cys Leu Glu Glu
                  100                 105                 110

Val Gly Trp Arg Arg Cys Ser Cys Ala Pro Gly Tyr Lys Leu Gly Asp
             115                 120                 125

Asp Leu Leu Gln Cys His Pro Ala Val Lys Phe Pro Cys Gly Arg Pro
        130                 135                 140

Trp Lys Arg Met Glu Lys Lys Arg Ser His Leu Lys Arg Asp Thr Glu
145              150                 155                 160

Asp Gln Glu Asp Gln Val Asp Pro Arg Leu Ile Asp Gly Lys Met Thr
                 165                 170                 175

Arg Arg Gly Asp Ser Pro Trp Gln Val Val Leu Leu Asp Ser Lys Lys
             180                 185                 190

Lys Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly

```
            210                 215                 220
Glu Tyr Asp Leu Arg Arg Trp Glu Lys Trp Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 5
caagtagatc cgcggctcat taacgggaag atgaccaggc gggg            44

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 6
ccccgcctgg tcatcttccc gttaatgagc cgcggatcta cttg            44

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 7
ctgacagcgg cccactgcat gaacgagtcc aagaagctcc ttgtc           45

<210> SEQ ID NO 8
<211> LENGTH: 45
```

```
<212> TYPE: DNA
<213> ORGANISM: Artificial Sequence
<220> FEATURE:
<223> OTHER INFORMATION: Description of Artificial Sequence: Primer

<400> SEQUENCE: 8
gacaaggagc ttcttggact cgttcatgca gtgggccgct gtcag            45

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 9
ctgacagcgg cccactgcat ggccgagtcc aagaagctcc ttgtc            45

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 10
gacaaggagc ttcttggact cggccatgca gtgggccgct gtcag            45

<210> SEQ ID NO 11
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 11
cttcgtccac cccaactaca gcaacagcac caccgacaat gacatc           46

<210> SEQ ID NO 12
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 12
gatgtcattg tcggtggtgc tgttgctgta gttggggtgg acgaag           46

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 13
cgtccacccc aactacagca agaacaccac cgacaatgac atcgc            45

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 14
```

```
gcgatgtcat tgtcggtggt gttcttgctg tagttggggt ggacg              45
```

<210> SEQ ID NO 15
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 15

```
ccctcgtgac gggctggggc aaccacagca gccgagagaa ggaggcc            47
```

<210> SEQ ID NO 16
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 16

```
ggcctccttc tctcggctgc tgtggttgcc ccagcccgtc acgaggg            47
```

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 17

```
cagcgaggtc atgagcaaca acgtgtctga gaacatgc                      38
```

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 18

```
gcatgttctc agacacgttg ttgctcatga cctcgctg                      38
```

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 19

```
gcagcgaggt catgagcaac gccgtgtctg agaacatgc                     39
```

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 20

```
gcatgttctc agacacggcg ttgctcatga cctcgctgc                     39
```

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 21
cccctggcag gtggtcctgc tgaactcaaa caagaagctg gcctgcgggg         50

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 22
ccccgcaggc cagcttcttg tttgagttca gcaggaccac ctgccagggg         50

<210> SEQ ID NO 23
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 23
cccctggcag gtggtcctgc tgaactcaac caagaagctg gcctgcgggg         50

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 24
ccccgcaggc cagcttcttg gttgagttca gcaggaccac ctgcc              45

<210> SEQ ID NO 25
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 25
ggcaggtggt cctgctggac aacaagacca agctggcctg cggggcagt          49

<210> SEQ ID NO 26
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 26
gcactgcccc gcaggccagc ttggtcttgt tgtccagcag gaccacctgc c        51

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 27
gtcctgctgg actcaaacaa gaccctggcc tgcggggcag tg                 42

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 28
cactgccccg caggccaggg tcttgtttga gtccagcagg ac                42

<210> SEQ ID NO 29
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 29
gcatggatga gtccaacaag acccttgtca ggcttggaga gtatgacc          48

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 30
ggtcatactc tccaagcctg acaagggtct tgttggactc atccatgc          48

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 31
ccaactacag caagagcaac accaccaatg acatcgcact gctgcacctg        50

<210> SEQ ID NO 32
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 32
gccaggtgca gcagtgcgat gtcattggtg gtgttgctct tgctgtagtt gg     52

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 33
ggctggggct accacagcaa ccgaaccaag gaggccaaga gaaaccgc          48

<210> SEQ ID NO 34
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 34
gcggtttctc ttggcctcct tggttcggtt gctgtggtag ccccagcc      48

<210> SEQ ID NO 35
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 35
ggctaccaca gcagccgaaa caagaccgcc aagagaaacc gcaccttcg     49

<210> SEQ ID NO 36
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 36
cgaaggtgcg gtttctcttg gcggtcttgt ttcggctgct gtggtagcc    49

<210> SEQ ID NO 37
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 37
gcagcgaggt catgaacaac accgtgtctg agaacatgct gtgtgcggg    49

<210> SEQ ID NO 38
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 38
cccgcacaca gcatgttctc agacacggtg ttgttcatga cctcgctgc    49

<210> SEQ ID NO 39
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 39
ggtgagctgg ggtgagggct gtgggaacct taccaactac ggcgtttaca cc    52

<210> SEQ ID NO 40
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 40
ggtgtaaacg ccgtagttgg taaggttccc acagccctca ccccagctca cc    52

<210> SEQ ID NO 41

```
<211> LENGTH: 6
<212> TYPE: PRT
<213> ORGANISM: Artificial Sequence
<220> FEATURE:
<223> OTHER INFORMATION: Description of Artificial Sequence: peptide tag

<400> SEQUENCE: 41

His His His His His His
 1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: peptide tag

<400> SEQUENCE: 42

Met Lys His His His His His His
 1               5

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: peptide tag

<400> SEQUENCE: 43

Met Lys His His Ala His His Gln His His
 1               5                  10

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: peptide tag

<400> SEQUENCE: 44

Met Lys His Gln His Gln His Gln His Gln His Gln His Gln
 1               5                  10

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: peptide tag

<400> SEQUENCE: 45

Met Lys His Gln His Gln His Gln His Gln His Gln His Gln Gln
 1               5                  10                  15

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: peptide tag

<400> SEQUENCE: 46

Glu Gln Lys Leu Ile Ser Glu Glu Asp Leu
 1               5                  10

<210> SEQ ID NO 47
<211> LENGTH: 8
```

```
<212> TYPE: PRT
<213> ORGANISM: Artificial Sequence
<220> FEATURE:
<223> OTHER INFORMATION: Description of Artificial Sequence: peptide tag

<400> SEQUENCE: 47

Asp Tyr Lys Asp Asp Asp Asp Lys
 1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: peptide tag

<400> SEQUENCE: 48

Tyr Pro Tyr Asp Val Pro Asp Tyr Ala
 1               5
```